US008067369B2

(12) United States Patent  
Gozes et al.

(10) Patent No.: US 8,067,369 B2
(45) Date of Patent: Nov. 29, 2011

(54) PROTECTION OF THE RETINA AGAINST LASER INJURY BY NAP AND RELATED PEPTIDES

(75) Inventors: Illana Gozes, Ramat Hasharon (IL); Michael Belkin, Givat Shmuel (IL)

(73) Assignee: Ramot at Tel-Aviv University, Tel-Aviv (IL)

( * ) Notice: Subject to any disclaimer, the term of this patent is extended or adjusted under 35 U.S.C. 154(b) by 225 days.

(21) Appl. No.: 12/280,471

(22) PCT Filed: Apr. 20, 2006

(86) PCT No.: PCT/IL2006/000481
§ 371 (c)(1), (2), (4) Date: Dec. 3, 2008

(87) PCT Pub. No.: WO2007/096859
PCT Pub. Date: Aug. 30, 2007

(65) Prior Publication Data
US 2009/0170780 A1    Jul. 2, 2009

Related U.S. Application Data

(60) Provisional application No. 60/776,329, filed on Feb. 24, 2006.

(51) Int. Cl.
*A61K 38/18* (2006.01)
*A61K 38/08* (2006.01)
(52) U.S. Cl. ...... 514/8.3; 514/17.7; 514/20.8; 514/21.3; 514/21.6; 514/21.7
(58) Field of Classification Search .................. None
See application file for complete search history.

(56) References Cited

U.S. PATENT DOCUMENTS

| | | | |
|---|---|---|---|
| 4,587,046 | A | 5/1986 | Goodman et al. |
| 5,198,420 | A | 3/1993 | Donahoe et al. |
| 5,556,757 | A | 9/1996 | Alstyne et al. |
| 5,767,240 | A | 6/1998 | Brenneman et al. |
| 6,113,947 | A | 9/2000 | Cleland et al. |
| 6,174,862 | B1 | 1/2001 | Brenneman |
| 6,613,740 | B1 | 9/2003 | Gozes et al. |
| 6,649,411 | B2 | 11/2003 | Gozes et al. |
| 6,933,277 | B2 | 8/2005 | Brenneman et al. |
| 7,264,947 | B2 | 9/2007 | Gozes et al. |
| 7,384,908 | B1 | 6/2008 | Brenneman et al. |
| 7,427,590 | B2 | 9/2008 | Brenneman et al. |
| 7,427,598 | B2 | 9/2008 | Spong et al. |
| 7,452,867 | B2 | 11/2008 | Gozes et al. |
| 7,863,247 | B1 | 1/2011 | Brenneman et al. |
| 2002/0028763 | A1 | 3/2002 | Shade et al. |
| 2002/0111301 | A1 | 8/2002 | Brenneman et al. |
| 2003/0166544 | A1 | 9/2003 | Clark et al. |
| 2004/0053313 | A1 | 3/2004 | Gozes et al. |
| 2007/0054847 | A1 | 3/2007 | Gozes et al. |
| 2008/0194488 | A1 | 8/2008 | Gozes et al. |
| 2009/0124543 | A1 | 5/2009 | Gozes et al. |
| 2009/0137469 | A1 | 5/2009 | Gozes et al. |
| 2009/0203615 | A1 | 8/2009 | Spong et al. |
| 2009/0247457 | A1 | 10/2009 | Brenneman et al. |
| 2010/0216723 | A1 | 8/2010 | Gozes et al. |

FOREIGN PATENT DOCUMENTS

| | | |
|---|---|---|
| EP | 1 206 489 B1 | 5/2004 |
| WO | WO 92/18140 A1 | 10/1992 |
| WO | WO 96/11948 A1 | 4/1996 |
| WO | WO 98/35042 A1 | 8/1998 |
| WO | WO 00/27875 A2 | 5/2000 |
| WO | WO 00/53217 A2 | 9/2000 |
| WO | WO 01/12654 A2 | 2/2001 |
| WO | WO 01/92333 A2 | 12/2001 |
| WO | WO 2004/080957 A2 | 9/2004 |

OTHER PUBLICATIONS

Levkovitch-Verbin 2002 (Investigative Ophthalmology & Visual Science 43:402-410).*
Nork et al. 2000 (Arch Ophthalmol 118:1242-1250).*
Bassan, M. et al. "VIP-Induced Mechanism of Neuroprotection: The Complete Sequence of a Femtomolar-Acting Activity-Dependent Neuroprotective Protein." *Regulatory Peptides*, vol. 71, No. 2, (Aug. 15, 1997).
Bedikian, Agop Y., et al., "Phase II Trial of Docetaxel in Patients with Advanced Cutaneous Malignant Melanoma Previously Untreated with Chemotherapy;" *Journal of Clinical Oncology* 13(12): 2895-2899 (Dec. 1995).
Bassan, M. et al. "Complete Sequence of a Novel Protein Containing a Femtomolar-Activity-Dependent Neuroprotective Peptide." *Journal of Neurochemistry* 72: 1283-1293 (1999).
Beni-Adani, L. et al. "Activity-Dependent Neurotrophic Protein is Neuroprotective in a Mouse Model of Closed Head Injury." Society for Neuroscience, 28th Annual Meeting, Los Angeles, CA, Nov. 7-12, 1998. *Abstracts*, vol. 24, Part 1, p. 1043 (1998).
Brenneman, D.E. and Gozes, I. "A Femtomolar-Acting Neuroprotective Peptide." *Journal of Clinical Investigation* 97:2299-2307 (1996).
Brenneman et al. "Neuronal Cell Killing by the Envelope Protein of HIV and Its Prevention by Vasoactive Intestinal Peptide," *Nature* 335:639 (1988).
Brenneman et al. "N-Methyl-D-Aspartate Receptors Influence Neuronal Survival in Developing Spinal Cord Cultures" *Dev. Brain Res.* 51:63 (1990).
Brenneman, D.E. et al. "Identification of a Nine Amino Acid Core Peptide from Activity Dependent Neurotrophic Factor I." Society for Neuroscience, 27th Annual Meeting, New Orleans, LA, Oct. 25-30, 1997. *Abstracts*, vol. 23, Part 2, p. 2250 (1997).
Brenneman, D.E. et al. "Activity-Dependent Neurotrophic Factor: Structure-Activity Relationships of Femtomolar-Acting Peptides." *Journal of Pharmacology and Experimental Therapeutics* 285:619-627 (1998).
Brenneman, D.E., et al.; "Protective Peptides Derived from Novel Glial Proteins;" *Biochemical Society Transactions* 28(4): 452-455 (2000).
Chiba, Tomohiro et al.; "Neuroprotective Effect of Activity-Dependent Neurotrophic Factor Against Toxicity From Familial Amyotrophic Lateral Sclerosis-Linked Mutant SOD1 in Vitro and in Vivo," *Journal of Neuroscience Research* 78:542-552 (2004).

(Continued)

*Primary Examiner* — Daniel E Kolker
(74) *Attorney, Agent, or Firm* — Kilpatrick Townsend & Stockton LLP

(57) ABSTRACT

This invention relates to the use of ADNF polypeptides in the treatment of laser-induced retinal damage and related conditions.

23 Claims, 6 Drawing Sheets

OTHER PUBLICATIONS

Chiba Tomohiro, et al., "Development of a Femtomolar-Acting Humanin Derivative Named Colivelin by Attaching Activity-Dependent Neurotrophic Factor to its N Terminus: Characterization of Colivelin-Mediated Neuroprotection against Alzheimer's Disease-Relevant Insults in Vitro and in Vivo;" *The Journal of Neuroscience* 25(44): 10252-10261 (Nov. 2, 2005).

Davidson, A. et al. "Protection Against Developmental Retardation and Learning Impairments in Apolipoprotein E-Deficient Mice by Activity-Dependent Femtomolar-Acting Peptides." Society for Neuroscience, 27th Annual Meeting, New Orleans, LA, Oct. 25-30, 1997. *Abstracts*, vol. 23, Part 2, p. 2250 (1997).

Dibbern, D.A., Jr. et al. "Inhibition of Murine Embryonic Growth by Human Immunodeficiency Virus Envelope Protein and Its Prevention by Vasoactive Intestinal Peptide and Activity-Dependent Neurotrophic Factor." *Journal of Clinical Investigation* 99:2837-2841 (1997).

Divinski, Irina, et al ., "A Femtomolar Acting Octapeptide Interacts with Tubulin and Protects Astrocytes Against Zinc Intoxication;" *The Journal of Biological Chemistry* 279(27):28531-28538 (Jul. 2, 2004).

Furman, Sharon, et al.; "Subcellular Localization and Secretion of Activity-Dependent Neuroprotective Protein in Astrocytes," *Neuron Glia Biology* 1:193-199 (2004).

GenBank Accession No. AB018327 from the DNA Data Bank of Japan (DDBJ) (released Nov. 17, 1998).

Giladi, E. "Protection Against Developmental and Learning Impairments in Apolipoprotein E-Deficient Mice by Activity-Dependent Femtomolar-Acting Peptides." *Neuroscience Letters*, Supplement 48 S1-S60, p. S19 (1997).

Glazner, G.W. et al. "A 9 Amino Acid Peptide Fragment of Activity-Dependent Neurotrophic Factor (ADNF) Protects Neurons from Oxidative Stress-Induced Death." Society for Neuroscience, 27th Annual Meeting, New Orleans, LA, Oct. 25-30, 1997. *Abstracts*, vol. 23, Part 2, p. 2249 (1997).

Glazner, G.W. at al. "Activity Dependent Neurotrophic Factor: A Potent Regulator of Embryonic Growth and Development," *Anat. Embryol*. 200:65-71 (1999).

Gozes, I. and Brenneman, D.E. "Activity-Dependent Neurotrophic Factor (ADNF)." *Journal of Molecular Neuroscience* 7:235-244 (1996).

Gozes, I. et al. "Stearyl-Norleucine-Vasoactive i/Intestinal Peptide (VIP): A novel VIP Analog for Noninvasive Impotence Treatment." *Endocrinology* 134:2125 (1994).

Gozes, I. et al. "Superactive Lipophilic Peptides Discriminate Multiple Vasoactive intestinal Peptide Receptors." *Journal of Pharmacology and Experimental Therapeutics* 273:161-167 (1995).

Gozes, I. et al. "Neuroprotective Strategy for Alzheimer Disease: Intranasal Administration of a Fatty Neuropeptide." *Proc. Natl. Acad. Sci. USA* 93:427-432 (1996).

Gozes I. et al. "Antiserum to Activity-Dependent Neurotrophic Factor Produces Neuronal Cell Death in CNS Cultures: Immunological and Biological Specificity." *Developmental Brain Research* 99:167-175 (1997).

Gozes, I. et al. A Femtomolar-Acting Activity-Dependent Neuroprotective Protein (ADNP). *Neuroscience Letters*, Supplement 48 S1-S60, p. S21 (1997).

Gozes, I. et al. "Protection Against Developmental Retardation in Apolipoprotein E-Deficient Mice by a Fatty neuropeptide: Implications for Early Treatment of Alzheimer's Disease." *Journal of Neurobiology* 33:329-342 (1997).

Gozes, I. et al. "The cDNA Structure of a Novel Femtomolar-Acting Neuroprotective Protein: Activity-Dependent-Neurotrophic Factor III (ADNFIII)." Society for Neuroscience, 27th Annual Meeting, New Orleans, LA, Oct. 25-30, 1997. *Abstracts*, vol. 23, Part 2, p. 2250 (1997).

Gozes, et al., "A Novel Signaling Molecule for Neuropeptide Action: Activity-dependent Neuroprotective Protein"; *Annals of the New York Academy of Sciences* 897:125-135 (1999).

Gozes, I. et al. "Activity-dependent neurotrophic factor: Intranasal administration of femtomolar-acting peptides improve performance in a water maze" *Journal of Pharmacology and Experimental Therapeutics* 293:1091-1098 (2000).

Gozes, Illana, "Tubulin in the Nervous System;" *Neurochemistry International* 4(23): 101-120 (1982).

Gozes, Illana and Divinski, Irina; "The Femtomolar-Acting NAP Interacts with Microtubules: Novel Aspects of Astrocyte Protection;" *Journal of Alzheimer's Disease* 6:S37-S41 (2004).

Gozes, Illana; "Tau as a Drug Target in Alzheimer's Diseaase;" *Journal of Molecular Neuroscience* 19: 337-338 (2002).

Gozes, Illana, et al.; "From Vasoactive Intestinal Peptide (VIP) Through Activity-Dependent Neuroprotective Protein (ADNP) to NAP," *Journal of Molecular Neuroscience* 20:315-322 (2003).

Gressens, P. et al. "Growth Factor Function of Vasoactive Intestinal Peptide in Whole Cultured Mouse Embryos." *Nature* 362:155-58 (1993).

Hannigan, J.H. and Berman, R.F. "Amelioration of Fetal Alcohol-Related Neurodevelopmental Disorders in Rats: Exploring Pharmacological and Environmental Treatments." *Neurotoxicol. & Teratol*. 22(1):103-111 (2000).

Hausheer et al., "Diagnosis, Management, and Evaluation of Chemotherapy-Induced Peripheral Neuropathy," *Semin. Oncol*. 33:15-49 (2006).

Hill, J.M. et al. "Learning Impairment in Adult Mice Produced by Early Embryonic Administration of Antiserum to Activity-Dependent Neurotrophic Factor (ADNF)." Society for Neuroscience, 27th Annual Meeting, New Orleans, LA, Oct. 25-30, 1997. *Abstracts*, vol. 23, Part 2, p. 2250 (1997).

Lagreze, Wolf A., et al.; "The Peptides ADNF-9 and NAP Increase Survival and Neurite Outgrowth of Rat Retinal Ganglion Cells in Vitro," *Investigative Opthalmology & Visual Science* 46(3):933-938 (Mar. 2005).

Lee, Virginia M.-Y., et al., "Transgenic Animal Models of Tauopathies;" *Biochimica et Biophysica Acta* 1739:251-259 (2005).

Lilling, G. et al. "Inhibition of Human Neuroblastoma Growth by a Specific VIP Antagonist." *Journal of Molecular Neuroscience* 5:231-239 (1995).

Mahato, R.I., et al. "Development of Targeted Delivery Systems for Nucleic Acid Drugs." *J. of Drug Targeting* 4(6):337-357 (1997) [Abstract].

McKune, S.K. et al. "Localization of mRNA for Activity-Dependent Neurotrophic Factor III (ADNF III) in Mouse Embryo and Adult CNS." Society for Neuroscience, 27th Annual Meeting, New Orleans, LA, Oct. 25-30, 1997. *Abstracts*, vol. 23, Part 2, p. 2249 (1997).

Nagase, T. et al., "Prediction of the Coding Sequences of Unidentified Human Genes. XI. The Complete Sequences of 100 New cDNA Clones from Brain Which Code for Large Proteins in vitro"; *DNA Research* 5:5:277-286 (1998).

Nelbock, P. et al. A cDNA for a Protein that Interacts with the Human Immunodeficiency Virus Tat Transactivator. *Science* 248:1650-1653 (1990).

Oberdoerster, J. et al. "The Effects of Ethanol on Neuronal Cell Death: Implications for the Fetal Alcohol Syndrome." *FASEB Journal* 12(4):A134 (Mar. 17, 1998).

Pelsman, A. et al. "In Vitro Degeneration of Down Syndrome Neurons is Prevented by Activity-Dependent Neurotrophic Factor-Derived Peptides." Society for Neuroscience, 28th Annual Meeting, Los Angeles, CA, Nov. 7-12, 1998. *Abstracts*, vol. 24, p. 1044 (1998).

Skolnick, J. and Fetrow, J.S. "From Genes to Protein Structure and Function: Novel Applications of Computational Approaches in the Genomic Era." *Trends in Biotech*. 18(1):34-39 (2000).

Smith, A.E. "Viral Vectors in Gene Therapy." *Ann. Rev.Microbiol*. 49:807-838 (1995) [Abstract].

Smith-Swintosky, Virginia L., et al., "Activity-Dependent Neurotrophic Factor-9 and NAP Promote Neurite Outgrowth in Rat Hippocampal and Cortical Cultures," *Journal of Molecular Neuroscience* 25:225-237 (2005).

Spinney, L. "New Peptides Prevent Brain Damage." *Molecular Medicine Today* 5(7):282 (Jul. 1999).

Spong, C.Y. et al. "Prevention of Fetal Alcohol Syndrome by Novel Peptides." *FASEB Journal* 13(5):A881 (Mar. 15, 1999).

Spong, C.Y. et al. "Prevention of Fetal Demise and Growth Restriction in a Mouse Model of Fetal Alcohol Syndrome" *The Journal of Pharmacology and Experimental Therapeutics* 297:774-779 (2001).

Stillman, M. and Cata, J.P., "Management of Chemotherapy-Induced Peripheral Neuropathy," *Curr. Pain Headache Rep.* 10:279-287, abstract only (2006).

Van Gool, S.W., et al.; "Disease-and Treatment-Related Elevation of the Neurodegenerative Marker Tau in Children with Hematological Malignancies," *Leukemia* 14:2076-2084 (2000).

Voet et al. *Biochemistry*, 2nd Ed., (New York, John Wiley & Sons., Inc.), p. 67, 1995.

Wilkemeyer, M.F. et al. "Differential effects of ethanol antagonism and neuroprotection in peptide fragment NAPVSIPQ prevention of ethanol-induced developmental toxicity," *PNAS* 100:8543-8548 (2003).

Yoles and Schwartz, "Degeneration of spared axons following partial white matter lesion: implications for optic nerve neuropathies," *Exp. Neurol.* 153:1-7 (1998).

Zemlyak, Ilona, et al.; "A Novel Peptide Prevents Death in Enriched Neuronal Cultures," *Regulatory Peptides* 96:39-43 (2000).

\* cited by examiner

SEQUENCE LISTING

<160> NUMBER OF SEQ ID NOS: 28

<210> SEQ ID NO 1
<211> LENGTH: 9
<212> TYPE: PRT
<213> ORGANISM: Artificial Sequence
<220> FEATURE:
<223> OTHER INFORMATION: ADNF I polypeptide active core site sequence;
    SAL

<400> SEQUENCE: 1

Ser Ala Leu Leu Arg Ser Ile Pro Ala
 1               5

<210> SEQ ID NO 2
<211> LENGTH: 8
<212> TYPE: PRT
<213> ORGANISM: Artificial Sequence
<220> FEATURE:
<223> OTHER INFORMATION: ADNF III polypeptide active core site sequence;
    NAP

<400> SEQUENCE: 2

Asn Ala Pro Val Ser Ile Pro Gln
 1               5

<210> SEQ ID NO 3
<211> LENGTH: 14
<212> TYPE: PRT
<213> ORGANISM: Artificial Sequence
<220> FEATURE:
<223> OTHER INFORMATION: ADNF I polypeptide sequence

<400> SEQUENCE: 3

Val Leu Gly Gly Gly Ser Ala Leu Leu Arg Ser Ile Pro Ala
 1               5                  10

<210> SEQ ID NO 4
<211> LENGTH: 19
<212> TYPE: PRT
<213> ORGANISM: Artificial Sequence
<220> FEATURE:
<223> OTHER INFORMATION: ADNF I polypeptide sequence

<400> SEQUENCE: 4

Val Glu Glu Gly Ile Val Leu Gly Gly Gly Ser Ala Leu Leu Arg Ser
 1               5                  10                  15

Ile Pro Ala

<210> SEQ ID NO 5
<211> LENGTH: 13
<212> TYPE: PRT
<213> ORGANISM: Artificial Sequence
<220> FEATURE:
<223> OTHER INFORMATION: ADNF I polypeptide sequence

<400> SEQUENCE: 5

Leu Gly Gly Gly Ser Ala Leu Leu Arg Ser Ile Pro Ala
 1               5                  10

<210> SEQ ID NO 6
<211> LENGTH: 12
<212> TYPE: PRT
<213> ORGANISM: Artificial Sequence
<220> FEATURE:
<223> OTHER INFORMATION: ADNF I polypeptide sequence

```
<400> SEQUENCE: 6

Gly Gly Gly Ser Ala Leu Leu Arg Ser Ile Pro Ala
 1               5                  10

<210> SEQ ID NO 7
<211> LENGTH: 11
<212> TYPE: PRT
<213> ORGANISM: Artificial Sequence
<220> FEATURE:
<223> OTHER INFORMATION: ADNF I polypeptide sequence

<400> SEQUENCE: 7

Gly Gly Ser Ala Leu Leu Arg Ser Ile Pro Ala
 1               5                  10

<210> SEQ ID NO 8
<211> LENGTH: 10
<212> TYPE: PRT
<213> ORGANISM: Artificial Sequence
<220> FEATURE:
<223> OTHER INFORMATION: ADNF I polypeptide sequence

<400> SEQUENCE: 8

Gly Ser Ala Leu Leu Arg Ser Ile Pro Ala
 1               5                  10

<210> SEQ ID NO 9
<211> LENGTH: 10
<212> TYPE: PRT
<213> ORGANISM: Artificial Sequence
<220> FEATURE:
<223> OTHER INFORMATION: ADNF III polypeptide sequence

<400> SEQUENCE: 9

Gly Gly Asn Ala Pro Val Ser Ile Pro Gln
 1               5                  10

<210> SEQ ID NO 10
<211> LENGTH: 13
<212> TYPE: PRT
<213> ORGANISM: Artificial Sequence
<220> FEATURE:
<223> OTHER INFORMATION: ADNF III polypeptide sequence

<400> SEQUENCE: 10

Leu Gly Gly Asn Ala Pro Val Ser Ile Pro Gln Gln Ser
 1               5                  10

<210> SEQ ID NO 11
<211> LENGTH: 15
<212> TYPE: PRT
<213> ORGANISM: Artificial Sequence
<220> FEATURE:
<223> OTHER INFORMATION: ADNF III polypeptide sequence

<400> SEQUENCE: 11

Leu Gly Leu Gly Gly Asn Ala Pro Val Ser Ile Pro Gln Gln Ser
 1               5                  10                  15

<210> SEQ ID NO 12
<211> LENGTH: 18
<212> TYPE: PRT
<213> ORGANISM: Artificial Sequence
<220> FEATURE:
<223> OTHER INFORMATION: ADNF III polypeptide sequence

<400> SEQUENCE: 12
```

Ser Val Arg Leu Gly Leu Gly Gly Asn Ala Pro Val Ser Ile Pro Gln
1               5                   10                  15

Gln Ser

<210> SEQ ID NO 13
<211> LENGTH: 88
<212> TYPE: PRT
<213> ORGANISM: Artificial Sequence
<220> FEATURE:
<223> OTHER INFORMATION: ADNF polypeptide sequence
<220> FEATURE:
<221> NAME/KEY: MOD_RES
<222> LOCATION: (1)...(40)
<223> OTHER INFORMATION: Xaa = any amino acid
<220> FEATURE:
<221> NAME/KEY: MOD_RES
<222> LOCATION: (1)...(40)
<223> OTHER INFORMATION: Xaa at positions 1-40 may be present or absent
<220> FEATURE:
<221> NAME/KEY: MOD_RES
<222> LOCATION: (49)...(88)
<223> OTHER INFORMATION: Xaa = any amino acid
<220> FEATURE:
<221> NAME/KEY: MOD_RES
<222> LOCATION: (49)...(88)
<223> OTHER INFORMATION: Xaa at positions 49-88 may be present or absent

<400> SEQUENCE: 13

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Asn Ala Pro Val Ser Ile Pro Gln
        35                  40                  45

Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa
            85

<210> SEQ ID NO 14
<211> LENGTH: 5
<212> TYPE: PRT
<213> ORGANISM: Artificial Sequence
<220> FEATURE:
<223> OTHER INFORMATION: ADNF peptide sequence

<400> SEQUENCE: 14

Val Leu Gly Gly Gly
1               5

<210> SEQ ID NO 15
<211> LENGTH: 5
<212> TYPE: PRT
<213> ORGANISM: Artificial Sequence
<220> FEATURE:
<223> OTHER INFORMATION: ADNF peptide sequence

<400> SEQUENCE: 15

Val Leu Gly Gly Gly
1               5

<210> SEQ ID NO 16
<211> LENGTH: 4
<212> TYPE: PRT

```
<213> ORGANISM: Artificial Sequence
<220> FEATURE:
<223> OTHER INFORMATION: ADNF peptide sequence

<400> SEQUENCE: 16

Val Leu Gly Gly
 1

<210> SEQ ID NO 17
<211> LENGTH: 5
<212> TYPE: PRT
<213> ORGANISM: Artificial Sequence
<220> FEATURE:
<223> OTHER INFORMATION: ADNF peptide sequence

<400> SEQUENCE: 17

Val Leu Gly Gly Gly
 1               5

<210> SEQ ID NO 18
<211> LENGTH: 5
<212> TYPE: PRT
<213> ORGANISM: Artificial Sequence
<220> FEATURE:
<223> OTHER INFORMATION: ADNF peptide sequence

<400> SEQUENCE: 18

Val Leu Gly Gly Val
 1               5

<210> SEQ ID NO 19
<211> LENGTH: 5
<212> TYPE: PRT
<213> ORGANISM: Artificial Sequence
<220> FEATURE:
<223> OTHER INFORMATION: ADNF peptide sequence

<400> SEQUENCE: 19

Val Leu Gly Gly Gly
 1               5

<210> SEQ ID NO 20
<211> LENGTH: 5
<212> TYPE: PRT
<213> ORGANISM: Artificial Sequence
<220> FEATURE:
<223> OTHER INFORMATION: ADNF peptide sequence

<400> SEQUENCE: 20

Gly Val Leu Gly Gly
 1               5

<210> SEQ ID NO 21
<211> LENGTH: 10
<212> TYPE: PRT
<213> ORGANISM: Artificial Sequence
<220> FEATURE:
<223> OTHER INFORMATION: ADNF I peptide sequence

<400> SEQUENCE: 21

Val Glu Glu Gly Ile Val Leu Gly Gly Gly
 1               5                  10

<210> SEQ ID NO 22
<211> LENGTH: 5
<212> TYPE: PRT
<213> ORGANISM: Artificial Sequence
<220> FEATURE:
```

```
<223> OTHER INFORMATION: ADNF III peptide sequence

<400> SEQUENCE: 22

Leu Gly Leu Gly Gly
 1               5

<210> SEQ ID NO 23
<211> LENGTH: 8
<212> TYPE: PRT
<213> ORGANISM: Artificial Sequence
<220> FEATURE:
<223> OTHER INFORMATION: ADNF III peptide sequence

<400> SEQUENCE: 23

Ser Val Arg Leu Gly Leu Gly Gly
 1               5

<210> SEQ ID NO 24
<211> LENGTH: 8
<212> TYPE: PRT
<213> ORGANISM: Artificial Sequence
<220> FEATURE:
<223> OTHER INFORMATION: NAP peptide sequence
<220> FEATURE:
<221> NAME/KEY: MOD_RES
<222> LOCATION: (1)...(1)
<223> OTHER INFORMATION: Xaa = 14C labeled Asn

<400> SEQUENCE: 24

Xaa Ala Pro Val Ser Ile Pro Gln
 1               5

<210> SEQ ID NO 25

<400> SEQUENCE: 25

000

<210> SEQ ID NO 26

<400> SEQUENCE: 26

000

<210> SEQ ID NO 27
<211> LENGTH: 89
<212> TYPE: PRT
<213> ORGANISM: Artificial Sequence
<220> FEATURE:
<223> OTHER INFORMATION: ADNF I polypeptide sequence
<220> FEATURE:
<221> NAME/KEY: MOD_RES
<222> LOCATION: (1)...(40)
<223> OTHER INFORMATION: Xaa = any amino acid
<220> FEATURE:
<221> NAME/KEY: MOD_RES
<222> LOCATION: (1)...(40)
<223> OTHER INFORMATION: Xaa at positions 1-40 may be present or absent
<220> FEATURE:
<221> NAME/KEY: MOD_RES
<222> LOCATION: (50)...(89)
<223> OTHER INFORMATION: Xaa = any amino acid
<220> FEATURE:
<221> NAME/KEY: MOD_RES
<222> LOCATION: (50)...(89)
<223> OTHER INFORMATION: Xaa at positions 50-89 may be present or absent

<400> SEQUENCE: 27

Xaa Xaa Xaa Xaa Xaa Xaa Xaa Xaa Xaa Xaa Xaa Xaa Xaa Xaa Xaa Xaa
 1               5                   10                  15
```

```
Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Ser Ala Leu Leu Arg Ser Ile Pro
        35                  40                  45

Ala Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa
                85

<210> SEQ ID NO 28
<211> LENGTH: 26
<212> TYPE: PRT
<213> ORGANISM: Artificial Sequence
<220> FEATURE:
<223> OTHER INFORMATION: SAL related peptide sequence

<400> SEQUENCE: 28

Ser Ala Leu Leu Arg Ser Ile Pro Ala Pro Ala Gly Ala Ser Arg Leu
1               5                   10                  15

Leu Leu Leu Thr Gly Glu Ile Asp Leu Pro
            20                  25
```

PROTECTION OF THE RETINA AGAINST LASER INJURY BY NAP AND RELATED PEPTIDES

This application is a U.S. National Phase Application under 35 U.S.C. §371 of International Application No. PCT/IL2006/000481, filed on Apr. 20, 2006, which claims the benefit of U.S. Provisional Application No. 60/776,329, filed Feb. 24, 2006, which is herein incorporated by reference for all purposes.

FIELD OF THE INVENTION

This invention relates to the use of ADNF polypeptides in the treatment of laser-induced retinal damage and other conditions involving retinal degeneration. The present invention also relates to the manufacture of medicaments, methods of formulation and uses thereof.

BACKGROUND OF THE INVENTION

In recent years, significant developments in laser technology have led to its application in the field of ophthalmic surgery. In particular, laser surgery has become the technique of choice for many ophthalmic surgical applications. While a number of common treatments involve purposeful retinal destruction (e.g., laser photocoagulation), other treatments may result in complications including retinal damage (P. L. Prendiville et al., Int. Ophthalmol. Clin. 32:179-204 (1992)). Accidental retinal damage has also been reported in ophthalmic practice (Y. Barkana et al., Surv. Ophthalmol, 44; 459-478 (2000)). In addition, laboratory, industrial and military use of lasers has led to many reported laser-induced eye injuries (H. F. Liu et al., Health. Phys. 56:711-716 (1989)). More recently, laser weapons aimed to damage electro-optical sensors and visually incapacitate soldiers by destroying parts of their retinas have been developed (Y. Barkana et al., 2000).

Retinal damage due to any of the foregoing causes typically triggers a process of secondary degeneration in neuronal cells adjacent to the primary lesion (E. Yoles et al., Exp. Neurol. 153:1-7 (1998)). This process of secondary degeneration starts by the release of noxious compounds from the primary lesion that subsequently spread and damage neighboring cells. The resulting damage to the retina, and corresponding functional consequences, are increased manifold by these secondary degeneration processes. Although there have been advances in the field, here remains a need for methods of treating, and minimizing, these secondary degeneration processes.

NAP, an 8-amino acid peptide (NAPVSIPQ=Asn-Ala-Pro-Val-Ser-Ile-Pro-Gln) (SEQ ID NO:2), is derived from a novel protein, activity-dependent neuroprotective protein, ADNP (U.S. Pat. No. 6,613,740; Bassan et al., J. Neurochem. 72: 1283-1293 (1999); Zamostiano, et al., J. Biol. Chem. 276: 708-714 (2001)). The NAP sequence within the ADNP gene is identical in rodents and humans (U.S. Pat. No. 6,613,740; Zamostiano, et al., J. Biol. Chem. 276:708-714 (2001)).

In cell cultures, NAP has been shown to have neuroprotective activity on cells of the central nervous system (CNS) at femtomolar concentrations (Bassan et al., 1999; Offen et al., Brain Res. 854:257-262 (2000)). Several animal models have also demonstrated NAP activity on diseases of the CNS. In animal models simulating parts of the Alzheimer's disease pathology, NAP was protective (Bassan et al., 1999; Gozes et al., J. Pharmacol. Exp. Ther. 293:1091-1098 (2000); see also U.S. Pat. No. 6,613,740). In normal aging rats, intranasal administration of NAP improved performance in the Morris water maze (Gozes et al., J. Mol. Neurosci. 19:175-178 (2002). NAP reduced infarct volume and motor unction deficits after ischemic injury, by decreasing apoptosis (Leker et al., Stroke 33:1085-1092 (2002)) and reducing damage caused by closed head injury in mice by decreasing inflammation (Beni Adani et al., J. Pharmacol. Exp. Ther. 296:57-63 (2001); Romano et al., J. Mol. Neurosci. 18:37-45 (2002); Zaltzman et al., NeuroReport 14:481-484 (2003)). NAP has been shown to provide protective intervention in a model of fetal alcohol syndrome, reducing fetal demise and growth restrictions (Spong et. al., J Pharmacol Exp Ther. 297.774-9 (2001)). Additionally, long term nasal NAP application in mice resulted in decreased anxiety (Alcalay et al., Neurosci Lett. 361(1-3):128-31 (2004)).

SAL, a 9-amino acid peptide (SALLRSIPA=Ser-Ala-Leu-Leu-Arg-Ser-Ile-Pro-Ala) (SEQ ID NO:1), also known as ADNF-9 or ADNF-1, was identified as the shortest active form of ADNF (see U.S. Pat. No. 6,174,862). SAL has been shown in in-vitro assays and in vivo disease models to keep neurons of the central nervous system alive in response to various insults (e.g., Gozes et al., 2000, infra; Brenneman et al., 1998. J. Pharmacol. Exp. Ther. 285, 619-627). D-SAL is an all D-amino acid derivative of SAL that is stable and orally available (Brenneman, el al., J Pharmacol Exp Ther. 309: 1190-7 (2004)) and surprisingly exhibits similar biological activity (potency and efficacy) to SAL in the systems tested. ADNF-1 complexes are described in International PCT Application No. PCT/US02/29146, filed Sep. 12, 2002 (published as WO03022226).

ADNF polypeptides, including NAP and SAL, and uses thereof in neuroprotection against disorders of the central nervous system, are the subject of numerous patents and patent applications including International PCT Publication No. WO01/92333, U.S. application Ser. No. 07/871,973 filed Apr. 22, 1992, now U.S. Pat. No. 5,767,240; U.S. application Ser. No. 08/342,297 filed Oct. 17, 1994 (published as WO96/11948), now U.S. Pat. No. 6,174,862; U.S. application Ser. No. 60/037,404 filed Feb. 7, 1997 published as WO98/35042); U.S. application Ser. No. 09/187,330 filed Nov. 11, 1998 (published as WO00/27875); U.S. application Ser. No. 09/267,511 filed Mar. 12, 1999 (published as WO00/53217); U.S. Pat. No. 6,613,740; U.S. application Ser. No. 60/149,956 filed Aug. 18, 1999 (published as WO01/12654); U.S. application Ser. No. 60/208,944 filed May 31, 2000; U.S. application Ser. No. 60/267,805 filed Feb. 8, 2001; International PCT Application No. PCT/IL2004/000232 filed Mar. 11, 2004 (published as WO 2004/080957); and International PCT Application No. PCT/US02/29146, filed Sep. 12, 2002 (published as WO 2003/022226); each of which are incorporated by reference in their entirety.

Given the increased use of lasers, both therapeutically and as weapons, improved methods of treating retinal damage caused by lasers are needed. The present invention solves his and other needs.

BRIEF SUMMARY OF THE INVENTION

As noted above, this disclosure provides new and surprising uses for ADNF polypeptides, including, for example, NAP, SAL, D-NAP and D-SAL, in the treatment of laser-induced retinal damage and other conditions involving retinal degeneration, including various ophthalmic diseases, such as glaucoma and ischemic optic neuropathy.

In one aspect, the present invention provides a method for treating laser-induced retinal damage in a subject, the method comprising administering a therapeutically effective amount of an ADNF polypeptide to a subject in need thereof.

In one embodiment, the ADNF polypeptide is a member selected from the group consisting of: (a) an ADNF I polypeptide comprising an active core site having the following amino acid sequence: Ser-Ala-Leu-Leu-Arg-Ser-Ile-Pro-Ala (SEQ ID NO: 1); (b) an ADNF III polypeptide comprising an active core site having the following amino acid sequence: Asn-Ala-Pro-Val-Ser-Ile-Pro-Gln (SEQ ID NO:2); and (c) a mixture of the ADNF I polypeptide of part (a) and the ADNF III polypeptide of part (b).

In a further embodiment, the ADNF polypeptide is a member selected from the group consisting of a full length ADNF I polypeptide, a fall length ADNF III polypeptide (ADNP), and a mixture of a full length ADNF I polypeptide and a fall length ADNF III polypeptide. In another further embodiment, the ADNF polypeptide is an ADNF I polypeptide.

In a more specific embodiment, the active core site of the ADNF I polypeptide comprises at least one D-amino acid.

In another more specific embodiment, the ADNF I polypeptide has the formula $(R^1)_x$-Ser-Ala-Leu-Leu-Arg-Ser-Ile-Pro-Ala-$(R^2)_y$ (SEQ ID NO:27) in which: (1) $R^1$ is an amino acid sequence comprising from 1 to about 40 amino acids wherein each amino acid is independently selected from the group consisting of naturally occurring amino acids and amino acid analogs; (2) $R^2$ is an amino acid sequence comprising from 1 to about 40 amino acids wherein each amino acid is independently selected from the group consisting of naturally occurring amino acids and amino acid analogs; and (3) x and y are independently selected and are equal to zero or one. ADNF I polypeptides can be additionally linked to other moieties such as alkyl or other lipophilic residues. Also included are ADNF-1 complexes, as described in International PCT Application No, PCT/US02/29146, filed Sep. 12, 2002 (published as WO 2003/022226).

In another more specific embodiment, the ADNF I polypeptide is Ser-Ala-Leu-Leu-Arg-Ser-Ile-Pro-Ala (SEQ ID NO:1).

In another more specific embodiment, the ADNF I polypeptide is selected from the group consisting of: Val-Leu-Gly-Gly-Gly-Ser-Ala-Leu-Leu-Arg-Ser-Ile-Pro-Ala (SEQ ID NO:3); Val-Glu-Glu-Gly-Ile-Val-Leu-Gly-Gly-Gly-Ser-Ala-Leu-Leu-Arg-Ser-Ile-Pro-Ala (SEQ ID NO:4); Leu-Gly-Gly-Gly-Ser-Ala-Leu-Leu-Arg-Ser-Ile-Pro-Ala (SEQ ID NO:5); Gly-Gly-Gly-Ser-Ala-Leu-Leu-Arg-Ser-Ile-Pro-Ala (SEQ ID NO:6); Gly-Gly-Ser-Ala-Lou-Leu-Arg-Ser-Ile-Pro-Ala (SEQ ID NO:7); Gly-Ser-Ala-Leu-Leu-Arg-Ser-Ile-Pro-Ala (SEQ ID NO:8); and Ser-Ala-Leu-Leu-Arg-Ser-Ile-Pro-Ala (SEQ ID NO:1).

In another more specific embodiment, the ADNF I polypeptide comprises up to about 20 amino acids at either or both of the N-terminus and the C-terminus of the active core site.

In another further embodiment, the ADNF polypeptide is an ADNF III polypeptide.

In a more specific embodiment, the active core site of the ADNF III polypeptide comprises at least one D-amino acid.

In another more specific embodiment, the ADNF III polypeptide has the formula $(R^1)_x$-Asn-Ala-Pro-Val-Ser-Ile-Pro-Gln-$(R^2)_y$ (SEQ ID NO:13) in which; (1) $R^1$ is an amino acid sequence comprising from 1 to about 40 amino acids wherein each amino acid is independently selected from the group consisting of naturally occurring amino acids and amino acid analogs; (2) $R^2$ is an amino acid sequence comprising from 1 to about 40 amino acids wherein each amino acid is independently selected from the group consisting of naturally occurring amino acids and amino acid analogs; and (3) x and y are independently selected and are equal to zero or one. ADNF III polypeptides can be additionally linked to other moieties such as alkyl or other lipophilic residues.

In another more specific embodiment, the ADNF III polypeptide is Asn-Ala-Pro-Val-Ser-Ile-Pro-Gln (SEQ ID NO:2).

In another more specific embodiment, the ADNF III polypeptide is a member selected from the group consisting of: Gly-Gly-Asn-Ala-Pro-Val-Ser-Ile-Pro-Gln (SEQ ID NO:9); Leu-Gly-Gly-Asn-Ala-Pro-Val-Ser-Ile-Pro-Gln-Gln-Ser (SEQ ID NO:10); Leu-Gly-Leu-Gly-Gly-Asn-Ala-Pro-Val-Ser-Ile-Pro-Gln-Gln-Ser (SEQ ID NO:11); Ser-Val-Arg-Leu-Gly-Leu-Gly-Gly-Asn-Ala-Pro-Val-Ser-Ile-Pro-Gln-Gln-Ser (SEQ ID NO:12); and Asn-Ala-Pro-Val-Ser-Ile-Pro-Gln (SEQ ID NO:2).

In another more specific embodiment, the ADNF III polypeptide comprises up to about 20 amino acids at either or both of the N-terminus and the C-terminus of the active core site.

In another further embodiment, a mixture of the ADNF I polypeptide of part (a) and the ADNF III polypeptide of part (b) are administered to the subject.

In a more specific embodiment, either or both active core sites of the ADNF I polypeptide and the ADNF III polypeptide comprise at least one D-amino acid.

In another more specific embodiment, the ADNF I polypeptide is Ser-Ala-Leu-Leu-Arg-Ser-Ile-Pro-Ala (SEQ ID NO:1), and the ADNF III polypeptide is Asn-Ala-Pro-Val-Ser-Ile-Pro-Gln (SEQ ID NO:2).

In another more specific embodiment, the ADNF I polypeptide is a member selected from the group consisting of: Val-Leu-Gly-Gly-Gly-Ser-Ala-Leu-Leu-Arg-Ser-Ile-Pro-Ala (SEQ ID NO:3); Val-Glu-Glu-Gly-Ile-Val-Leu-Gly-Gly-Gly-Ser-Ala-Leu-Leu-Arg-Ser-Ile-Pro-Ala (SEQ ID NO:4); Leu-Gly-Gly-Gly-Ser-Ala-Leu-Leu-Arg-Ser-Ile-Pro-Ala (SEQ ID NO:5); Gly-Gly-Gly-Ser-Ala-Leu-Leu-Arg-Ser-Ile-Pro-Ala (SEQ ID NO:6); Gly-Gly-Ser-Ala-Leu-Leu-Arg-Ser-Ile-Pro-Ala (SEQ ID NO:7); Gly-Ser-Ala-Leu-Leu-Arg-Ser-Ile-Pro-Ala (SEQ ID NO:8); and Ser-Ala-Leu-Leu-Arg-Ser-Ile-Pro-Ala (SEQ ID NO: 1), and the ADNF III polypeptide is selected from the group consisting of: Gly-Gly-Asn-Ala-Pro-Val-Ser-Ile-Pro-Gln (SEQ ID NO:9); Leu-Gly-Gly-Asn-Ala-Pro-Val-Ser-Ile-Pro-Gln-Gln-Ser (SEQ ID NO:10); Leu-Gly-Leu-Gly-Gly-Asn-Ala-Pro-Val-Ser-Ile-Pro-Gln-Gln-Ser (SEQ) ID NO:11); Ser-Val-Arg-Leu-Gly-Leu-Gly-Gly-Asn-Ala-Pro-Val-Ser-Ile-Pro-Gln-Gln-Ser (SEQ ID NO:12); and Asn-Ala-Pro-Val-Ser-Ile-Pro-Gln (SEQ ID NO:2).

In another more specific embodiment, the ADNF I polypeptide comprises up to about 20 amino acids at either or both of the N-terminus and the C-terminus of the active core site of the ADNF I polypeptide, and the ADNF III polypeptide comprises up to about 20 amino acids at either or both of the N-terminus and the C-terminus of the active core site of the ADNF III polypeptide.

In another further embodiment, the ADNF polypeptide is administered intranasally, orally, intravenously, subcutaneously, intravitreally or topically, e.g. using eye drops.

In another further embodiment, the laser-induced retinal damage is a consequence of laser photocoagulation.

In a preferred embodiment, the ADNF polypeptide is administered topically, e.g. using eye drops.

These and other aspects of the invention will be evident upon reference to the following detailed description and attached drawings.

DETAILED DESCRIPTION OF THE INVENTION

Definitions

Figure 1A:
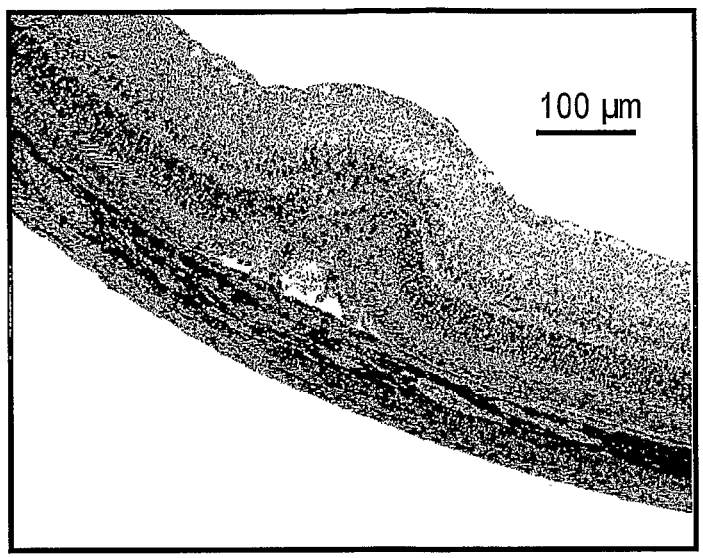
FIGS. 1a-1c show microscopic views of an untreated laser lesion 3, 20, and 60 days after laser irradiation.

The phrase "ADNF polypeptide" refers to one or more activity dependent neurotrophic factors (ADNF) that have an active core site comprising the amino acid sequence of SALLRSIPA (referred to as "SAL"; SEQ ID NO:1) or NAPVSIPQ (referred to as "NAP"; SEQ ID NO:2), or conservatively modified variants thereof that have neurotrophic/neuroprotective activity as measured with in vitro cortical neuron culture assays described by, e.g., Hill et al., *Brain Res.* 603: 222-233 (1993); Brenneman & Gozes, *J. Clin. Invest.* 97:2299-2307 (1996), Gozes et al., *Proc. Natl. Acad. Sci. USA* 93, 427-432 (1996). An ADNF polypeptide can be an ADNF I polypeptide, an ADNF III polypeptide, their alleles, polymorphic variants, analogs, interspecies homolog, any subsequences thereof (e.g., SALLRSIPA; SEQ ID NO:1 or NAPVSIPQ; SEQ ID NO:2) or lipophilic variants that exhibit neuroprotective/neurotrophic action on, e.g., neurons originating in the central nervous system either in vitro or in vivo. An "ADNF polypeptide" can also refer to a mixture of an ADNF I polypeptide and an ADNF III polypeptide.

The terms "ADNF I polypeptide" and "ADNF I" refer to an activity dependent neurotrophic factor polypeptide having a molecular weight of about 14,000 Daltons with a pI of 8.3±0.25. As described above, ADNF I polypeptides have an active site comprising an amino acid sequence of Ser-Ala-Leu-Leu-Arg-Ser-Ile-Pro-Ala (also referred to as "SALLR-SIPA" or "SAL" or "ADNF-9"; SEQ ID NO:1). See Brenneman & Gozes, *J. Clin. Invest.* 97:2299-2307 (1996), Glazner et al., *Anat. Embryol.* 200:65-71 (1999), Brenneman et al., *J. Pharm. Exp. Ther.*, 285:619-27 (1998), Gozes & Brenneman, *J. Mol. Neurosci.* 7:235-244 (1996), and Gozes et al., *Dev. Brain Res.* 99:167-175 (1997). Unless indicated as otherwise, "SAL" refers to a peptide having an amino acid sequence of Ser-Ala-Leu-Leu-Arg-Ser-Ile-Pro-Ala (SEQ ID NO:1), not a peptide having an amino acid sequence of Ser-Ala-Leu. A full length amino acid sequence of ADNF I can be found in International PCT Publication No. WO 96/11948.

The terms "ADNF III polypeptide" and "ADNF III" also called activity-dependent neuroprotective protein (ADNP) refer to one or more activity dependent neurotrophic factors (ADNF) that have an active core site comprising the amino acid sequence of NAPVSIPQ (referred to as "NAP"; SEQ ID NO:2), or conservatively modified variants thereof that have neurotrophic/neuroprotective activity as measured with in vitro cortical neuron culture assays described by, e.g., Hill et al., *Brain Res.* 603, 222-23.3 (1993); Gozes et al., *Proc. Natl. Acad. Sci. USA* 93, 427-432 (1996). An ADNF polypeptide can be an ADNF III polypeptide, allelic or polymorphic variant, analog, interspecies homolog, or any subsequences thereof (e.g., NAPVSIPQ; SEQ ID NO:2) that exhibit neuroprotective/neurotrophic action on, e.g., neurons originating in the central nervous system either in vitro or in vivo. ADNF III polypeptides can range from about eight amino acids and can have, e.g., between 8-20, 8-50, 10-100 or about 1000 or more amino acids.

Full length human ADNF III has a predicted molecular weight of 123,562.8 Da (>1000 amino acid residues) and a pI of about 6.97. As described above, ADNF III polypeptides have an active site comprising an amino acid sequence of Asn-Ala-Pro-Val-Ser-Ile-Pro-Gln (also referred to as "NAPVSIPQ" or "NAP"; SEQ ID NO:2). See Zamostiano et al., *J. Biol. Chem.* 276:708-714 (2001) and Bassan et al., *J. Neurochem.* 72:1283-1293 (1999). Unless indicated as otherwise, "NAP" refers to a peptide having an amino acid sequence of Asn-Ala-Pro-Val-Ser-Ile-Pro-Gln (SEQ ID NO:2), not a peptide having an amino acid sequence of Asn-Ala-Pro. Full-length amino acid and nucleic acid sequences of ADNF III can be found in International PCT Publication Nos. WO 98/35042 and WO 00/27875, and U.S. Pat. No. 6,613,740. The Accession number for the human sequence is NP_852107, see also Zamostiano et al., infra.

The term "amino acid" refers to naturally occurring and synthetic amino acids, as Well as amino acid analogs and amino acid mimetics that function in a manner similar to the naturally occurring amino acids. Naturally occurring amino acids are those encoded by the genetic code, as well as those amino acids that are later modified, e.g. hydroxyproline, γ-carboxyglutamate, and O-phosphoserine. For the purposes of this application, amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. For the purposes of this application, amino acid mimetics refers to chemical compounds that have a structure that is different from the general chemical structure of an amino acid, but that functions in a manner similar to a naturally occurring amino acid.

Amino acids may include those having non-naturally occurring D-chirality, as disclosed in international PCT Publication No. WO 01/12654, incorporated herein by reference, which may improve oral availability and other drug like characteristics of the compound. In such embodiments, one or more, and potentially all of the amino acids of NAP or the ADNF polypeptide will have D-chirality. The therapeutic use of peptides can be enhanced by using D-amino acids to provide longer half life and duration of action. However, many receptors exhibit a strong preference for L-amino acids, but examples of D-peptides have been reported that have equivalent activity to the naturally occurring L-peptides, for example, pore-forming antibiotic peptides, beta amyloid peptide (no change in toxicity), and endogenous ligands for the CXCR4 receptor. In this regard, NAP and ADNF polypeptides also retain activity in the D-amino acid form (Brenneman et al., *J. Pharmacol. Exp. Ther.* 309(3):1190-7 (2004), infra).

Amino acids may be referred to by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8; 91-98 (1994)). Because of the degeneracy of the genetic code, a large number of functionally identical nucleic acids encode any given protein. For instance, the codons GCA, GCC, GCG and GCU all encode the amino acid alanine. Thus, at every position where al alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following groups each contain amino acids that are conservative substitutions for one another:

1) Alanine (A), Glycine (G);
2) Serine (S), Threonine (T);
3) Aspartic acid (D), Glutamic acid (E);
4) Asparagine (N), Glutamine (Q);
5) Cysteine (C), Methionine (M);
6) Arginine (R), Lysine (K), Histidine (P);
7) Isoleucine (I), Leucine (L), Valine (V); and
8) Phenylalanine (F), Tyrosine (Y), Tryptophan (W). (see, e.g., Creighton, *Proteins* (1984)).

The terms "polypeptide," "peptide" and "protein" are used interchangeably herein to refer to a polymer of amino acid residues. Generally, a peptide refers to a short polypeptide. The terms apply to amino acid polymers in which one or more amino acid residue is an analog or mimetic of a corresponding naturally occurring amino acid, as well as to naturally occurring amino acid polymers.

"Nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. The term nucleic acid is used interchangeably with gene, cDNA, mRNA, oligonucleotide, and polynucleotide.

The term "subject" refers to any mammal, in particular human, at any stage of life.

The term "contacting" is used herein interchangeably with the following: combined with, added to, mixed with, passed over, incubated with, flowed over, etc. Moreover, the ADNF polypeptides or nucleic acids encoding them of the present invention can be "administered" by any conventional method such as, for example, parenteral (e.g., intravenous, subcutaneous, intradermally or intramuscularly), oral, topical, intravitreal and inhalation (e.g., intranasal) routes.

As used heroin "treatment" includes preventative treatment or prophylaxis, such as treatment for prevention of disease progression or onset of further symptoms, or for avoidance or reduction of side-effects or symptoms of a disease.

As used herein, "condition" and "disease" include incipient conditions or disorders, or symptoms of a disease, incipient condition or disorder.

The terms "isolated," "purified" or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. In particular, an isolated ADNF nucleic acid is separated from open reading frames that flank the ADNF gene and encode proteins other than ADNF. The term "purified" denotes that a nucleic acid or protein gives rise to essentially one band in an electrophoretic gel. Particularly, it means that the nucleic acid or protein is at least 85% pure, more preferably at least 95% pure, and more preferably at least 99% pure.

"An amount sufficient" or "an effective amount" or a "therapeutically effective amount" is that amount of an ADNF polypeptide that exhibits the activity of interest or which provides either a subjective relief of a symptom(s) or an objectively identifiable improvement as noted by the clinician or other qualified observer. In therapeutic applications, the ADNF polypeptides of the invention are administered to a patient in an amount sufficient to reduce or eliminate symptoms of the disease or condition. An amount adequate to accomplish this is defined as the "therapeutically effective dose." The dosing range varies with the ADNF polypeptide used, the route of administration and the potency of the particular ADNF polypeptide, as further set out below, and as described in patents CA Patent No. 2202496, U.S. Pat. No. 6,174,862 and U.S. Pat. No. 6,613,740.

As used herein "laser-induced retinal damage" includes both intentional and accidental retinal damage resulting from laser exposure.

"Laser photocoagulation" refers to a surgical procedure wherein a laser is used to seal leaking blood vessels within the retina and reduce the future growth of abnormal blood vessels. By sealing leaking blood vessels, laser photocoagulation slows down, e.g., the buildup of fluid under the retina that distorts the shape and position of the macula, the growth of scar tissue and the abnormal membrane under the retina that damage the cells in the macula, and central vision loss.

"Conditions involving retinal degeneration" include, but are not limited to, laser-induced retinal damage and ophthalmic diseases, such as glaucoma, Retinitis pigmentosa, Usher syndrome, artery or vein occlusion, diabetic retinopathy, retrolental fibroplasias or retinopathy of prematurity (R.L.F./R.O.P.), retinoschisis, lattic degeneration, macular degeneration and ischemic optic neuropathy.

This invention discloses the surprising finding that ADNF polypeptides that were shown previously to be neuroprotective of the CNS and to provide cognitive enhancement can also be used in the treatment of laser-induced retinal damage and other conditions involving retinal degeneration. The invention is supported by the findings set out in the Examples that in vivo administration of NAP significantly reduces the spread of laser-induced retinal damage by secondary retinal degeneration processes.

ADNF Polypeptides: Composition and Synthesis

In one embodiment, the ADNF polypeptides of the present invention comprise the following amino acid sequence: $(R^1)_x$-Asn-Ala-Pro-Val-Ser-Ile-Pro-Gln-$(R^2)_y$ (SEQ ID NO:13) and conservatively modified variations thereof. In this designation, $R^1$ denotes the orientation of the amino terminal ($NH_2$ or N-terminal) end and $R^2$ represents the orientation of the carboxyl terminal (COOH or C-terminal) end.

In the above formula, $R^1$ is an amino acid sequence comprising from 1 to about 40 amino acids, wherein each amino acid is independently selected from the group consisting of naturally occurring amino acids and amino acid analogs. The term "independently selected" is used herein to indicate that the amino acids making up the amino acid sequence $R^1$ may be identical or different (e.g., all of the amino acids in the amino acid sequence may be threonine, etc.). Moreover, as previously explained, the amino acids making up the amino acid sequence $R^1$ may be either naturally occurring amino acids, or known analogs of natural amino acids that functions in a manner similar to the naturally occurring amino acids (i.e., amino acid mimetics and analogs).

As with $R^1$, $R^2$, in the above formula, is an amino acid sequence comprising from 1 to about 40 amino acids, wherein each amino acid is independently selected from the group consisting of naturally occurring amino acids and amino acid analogs. Moreover, as with $R^1$, the amino acids making up the amino acid sequence $R^2$ may be identical or different, and may be either naturally occurring amino acids, or known analogs of natural amino acids that functions in a manner similar to the naturally occurring amino acids (i.e., amino acid mimetics and analogs).

Within the above formula, x and y are independently selected and are equal to zero or one. The term independently selected is used herein to indicate that x and y may be identical or different. For example, x and y may both be zero or, alternatively, x and y may both be one. In addition, x may be zero and y may be one or, alternatively, x may be one and y may be zero.

As used herein, "NAP" or "NAP peptide" refers to the formula above where x and y both equal 0. "NAP related peptide" refers to any of the other variants of NAP which are described by the formula.

$R^1$ and $R^2$ are independently selected. If $R^1$ and $R^2$ are the same, they are identical in terms of both chain length and amino acid composition. For example, both $R^1$ and $R^2$ may be Val-Leu-Gly-Gly-Gly (SEQ ID NO:14). If $R^1$ and $R^2$ are different, they can differ from one another in terms of chain length and/or amino acid composition and/or order of amino acids in the amino acids sequences. For example, $R^1$ may be Val-Leu-Gly-Gly-Gly (SEQ ID NO:15), whereas $R^2$ may be Val-Leu-Gly-Gly (SEQ ID NO:16). Alternatively, $R^1$ may be Val-Leu-Gly-Gly-Gly (SEQ ID NO:17), whereas $R^2$ may be Val-Leu-Gly-Gly-Val (SEQ ID NO:18). Alternatively, $R^1$ may be Val-Leu-Gly-Gly-Gly (SEQ ID NO:19), whereas $R^2$ may be Gly-Val-Leu-Gly-Gly (SEQ ID NO:20).

In another embodiment, the ADNF polypeptide comprises the following amino acid sequence: $(R^1)_x$-Ser-Ala-Leu-Leu-Arg-Ser-Ile-Pro-Ala-$(R^2)_y$ (SEQ ID NO:27) and conservatively modified variations thereof. In this designation, $R^1$ denotes the orientation of the amino terminal ($NH_2$ or N-terminal) end and $R^2$ represents the orientation of the carboxyl terminal (COOH or C-terminal) end.

In the above formula, $R^1$ is an amino acid sequence comprising from 1 to about 40 amino acids, wherein each amino acid is independently selected from the group consisting of naturally occurring amino acids and amino acid analogs. The term "independently selected" is used herein to indicate that the amino acids making up the amino acid sequence $R^1$ may be identical or different (e.g., all of the amino acids in the amino acid sequence may be threonine, etc.). Moreover, as previously explained, the amino acids making up the amino acid sequence $R^1$ may be either naturally occurring amino acids, or known analogs of natural amino acids that functions in a manner similar to the naturally occurring amino acids (i.e., amino acid mimetics and analogs).

As with $R^1$, $R^2$, in the above formula, is an amino acid sequence comprising from 1 to about 40 amino acids, wherein each amino acid is independently selected from the group consisting of naturally occurring amino acids and amino acid analogs. Moreover, as with $R^1$, the amino acids making up the amino acid sequence $R^2$ may be identical or different, and may be either naturally occurring amino acids, or known analogs of natural amino acids that functions in a manner similar to the naturally occurring amino acids (i.e., amino acid mimetics and analogs).

Within the above formula, x and y are independently selected and are equal to zero or one. The term independently selected is used herein to indicate that x and y may be identical or different. For example, x and y may both be zero or, alternatively, x and y may both be one. In addition, x may be zero and y may be one or, alternatively, x may be one and y may be zero.

As used herein, "SAL" or "SAL peptide" refers to the formula above where x and y both equal 0. "SAL related peptide" refers to any of the other variants of SAL which are described by the formula.

Similar to the previous embodiment, in the above formula, $R^1$ and $R^2$ are independently selected. If $R^1$ and $R^2$ are the same, they are identical in terms of both chain length and amino acid composition.

Within the scope of the above formulas, certain ADNF I and ADNF III polypeptides are preferred, namely those in which x and y are both zero (i.e., SALLRSIPA, SEQ ID NO:1, and NAPVSIPQ, SEQ ID NO:2, respectively). Equally preferred are ADNF I polypeptides in which x is one; $R^1$ is Val-Leu-Gly-Gly-Gly (SEQ ID NO:15); and y is zero. Also equally preferred are ADNF I polypeptides in which x is one; $R^1$ is Val-Glu-Glu-Gly-Ile-Val-Leu-Gly-Gly-Gly (SEQ ID NO:21); and y is zero. Also equally preferred are ADNF III polypeptides in which w is one; $R^1$ is Gly-Gly; and z is zero. Also equally preferred are ADNF III polypeptides in which w is one; $R^1$ is Leu-Gly-Gly; z is one; and $R^2$ is Gln-Ser. Also equally preferred are ADNF III polypeptides in which w is one; $R^1$ is Leu-Gly-Leu-Gly-Gly- (SEQ ID NO:22); z is one; and $R^2$ is Gln-Ser. Also equally preferred are ADNF III polypeptides in which w is one; $R^1$ is Ser-Val-Arg-Leu-Gly-Leu-Gly-Gly (SEQ ID NO:23); z is one; and $R^2$ is Gln-Ser. Additional amino acids can be added to both the N-terminus and the C-terminus of these active sites (SALLRSIPA, SEQ ID NO:1, or NAPVSIPQ, SEQ ID NO:2) without loss of biological activity as evidenced by the fact that the intact ADNF I or ADNF III growth factors exhibit extraordinary biological activity. See, U.S. application Ser. No. 08/324,297, filed Oct. 17, 1994 (also published as International PCT Publication No. WO96/11948) for the description of ADNF I polypeptides; and U.S. Application No. 60/037,404 filed Feb. 27, 1997 and U.S. Application No. 60/059,621 filed, Sep. 23, 1997 (also published as International PCT Publication No. WO98/35042) for the description of ADNF III polypeptides, all of which are incorporated herein by reference.

In another aspect, the present invention provides pharmaceutical compositions comprising one of the previously described NAP and NAP related polypeptides in an amount sufficient to exhibit desired therapeutic activity, in a pharmaceutically acceptable diluent, carrier or excipient. In one embodiment, the NAP or NAP related peptide has an amino acid sequence selected from the group consisting of SEQ ID NO:2, and 9-12, and conservatively modified variations thereof.

In another aspect, the present invention provides pharmaceutical compositions comprising one of the previously described SAL and SAL-related polypeptides in an amount sufficient to desired therapeutic activity, in a pharmaceutically acceptable diluent, carrier or excipient. In one embodiment, the SAL or SAL related peptide has an amino acid sequence selected from the group consisting of SEQ ID NO:1 and 3-8, and conservatively modified variations thereof.

In a further embodiment, the SAL related peptide comprises SALLRSIPAPAGASRLLLLTGEIDLP (SEQ ID NO:28). This sequence (SEQ ID NO:28) is also known as Colivelin and is a combination of the SAL active site and a derivative of the Humanin protein named AGA-(C8R) HNG17. Colivelin is described in Chiba et al., *J. Neurosci.* 25:10252-10261 (2005), which is herein incorporated by reference for all purposes.

It will be readily apparent to those of ordinary skill in the art that preferred ADNF polypeptides can readily be selected for their desired activity by employing suitable assays and animal models known to those skilled in the art, some of which are disclosed herein.

In addition, one of skill in the art will recognize that a variety of chemical modifications can be made to the peptides without diminishing their biological activity. In addition to replacement of specific amino acids with other amino acids, there may also be a wide range of modifications to specific amino acids, and conjugates with a wide variety of polymers, proteins, carbohydrates or other organic moieties.

The peptides of the invention may be prepared via a wide variety of well-known techniques. Peptides of relatively short size are typically synthesized on a solid support or in solution in accordance with conventional techniques (see, e.g., Merrifield, *Am. Chem. Soc.* 85:2149-2154 (1963)). Various automatic synthesizers and sequencers are commercially available and can be used in accordance with known protocols (see, e.g., Stewart & Young, *Solid Phase Peptide Synthesis* (2nd ed. 1984)). Solid phase synthesis in which the C-terminal amino acid of the sequence is attached to an insoluble support followed by sequential addition of the remaining amino acids in the sequence is the preferred method for the chemical synthesis of the peptides of this invention. Techniques for solid phase synthesis are described by Barany & Merrifield, *Solid-Phase Peptide Synthesis*; pp. 3-284 in *The Peptides: Analysis, Synthesis, Biology*. Vol. 2: *Special Methods in Peptide Synthesis*, Part A; Merrifield et al 1963; Stewart et al. 1984) NAP and related peptides are synthesized using standard Fmoc protocols (Wellings & Atherton, *Methods Enzymol.* 289:44-67 (1997)).

Other synthetic methods for peptides include liquid phase synthesis (e.g. Fischer and Zheleva *J Pept Sci.* 8(9):529-42 (2002).

In addition to the foregoing techniques, the ADNF peptides, in particular the full length proteins ADNF I and ADNF III for use in the invention may be prepared by recombinant DNA methodology. Generally, this involves creating a nucleic acid sequence that encodes the protein, placing the nucleic acid in an expression cassette under the control of a particular promoter, and expressing the protein in a host cell. Recombinantly engineered cells known to those of skill in the art include, but are not limited to, bacteria, yeast, plant, filamentous fungi, insect (especially employing baculoviral vectors) and mammalian cells.

Pharmaceutical Administration

ADNF polypeptides and nucleic acids encoding ADNF polypeptides can be administered to a subject using any suitable methods known in the art. See, e.g., Gozes, et al., Trends in Neuroscience, 24(12):700-705 (2001); Gozes, et al., J. Molec. Neurosci. 19:167-170 (2002); Leker, et al., Stroke, 33(4):1085-1092 (2002); Gozes, et al., "Intranasal delivery of bioactive peptides or peptide analogues enhances spatial memory and protects against cholinergic deficits" In: The Proceedings of the 44th Oholo Conference; The Blood Brain Barrier Drug Delivery and Brain Pathology. 363-370. For example, ADNF polypeptides or nucleic acids can be formulated as pharmaceutical compositions with a pharmaceutically acceptable diluent, carrier or excipient. Suitable formulations for use in the present invention are found in Remington's Pharmaceutical Sciences (17th ed. 1985)), which is incorporated herein by reference. A brief review of methods for drug delivery is also described in, e.g., Langer, Science 249:1527-1533 (1990), which is incorporated herein by reference. In addition, pharmaceutical compositions comprising peptides and proteins are described in, e.g., Therapeutic Peptides and Proteins Formulations, Processing, and Delivery Systems, by Banga, Technomic Publishing Company, Inc., Lancaster, Pa. (1995).

ADNF polypeptides can be administered in any pharmaceutically acceptable composition. A pharmaceutically acceptable nontoxic composition is formed by incorporating any of normally employed excipients, and generally 10-95% of active ingredient and more preferably at a concentration of 25%-75%. Furthermore, to improve oral absorption of ADNF polypeptides, various carrier systems, such as nanoparticles, microparticles, liposomes, phospholipids, emulsions, erythrocytes, etc. can be used. The oral agents comprising ADNF polypeptides of the invention can be in any suitable form for oral administration, such as liquid, tablets, capsules, or the like. The oral formulations can be further coated or treated to prevent or reduce dissolution in stomach. See, e.g., Therapeutic Peptides and Proteins, Formulation, Processing, and Delivery Systems, by A. K. Banga, Technomic Publishing Company, Inc., 1995.

Furthermore, the ADNF polypeptides can be formulated for parenteral (e.g., intravenous, subcutaneous, intradermally or intramuscularly), topical, intravitreal and inhalation (e.g., intranasal) administration. Thus, the invention provides compositions for parenteral administration that comprise a solution of a single or mixture of ADNF polypeptides, dissolved or suspended in an acceptable carrier, preferably an aqueous carrier. A variety of aqueous carriers may be used including, for example, water, buffered water, 0.4% saline, 0.3% glycine, hyaluronic acid and the like. These compositions may be sterilized by conventional, well known sterilization techniques, or they may be sterile filtered. The resulting aqueous solutions may be packaged for use as is or lyophilized, the lyophilized preparation being combined with a sterile solution prior to administration. The compositions may contain pharmaceutically acceptable auxiliary substances as required to approximate physiological conditions including pH adjusting and buffering agents, tonicity adjusting agents, wetting agents and the like, such as, for example, sodium acetate, sodium lactate, sodium chloride, potassium chloride, calcium chloride, sorbitan monolaurate, triethanolamine oleate, etc.

For aerosol administration, ADNF polypeptides are preferably supplied in finely divided form along with a surfactant and propellant. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. A carrier can also be included, as desired, as with, e.g., lecithin for intranasal delivery.

For solid compositions, conventional nontoxic solid carriers may be used. Solid carriers include, for example, pharmaceutical grades of mannitol, lactose, starch, magnesium stearate, sodium saccharin, talcum, cellulose, glucose, sucrose, magnesium carbonate, and the like.

For intravitreal administration, ADNF polypeptides are preferably administered in a vehicle containing saline, ADNF polypeptides can also be administered topically, e.g., using eye drops. For eye drop formulation the active compound may be dissolved in 150 mM NaCl, 10 mM HEPES buffer pH 8.0 supplemented with 0.5% sodium caprate (Sigma Chemical Company, St Louis, Mo., USA) to enhance penetration of the protein 5, 6 and 1.5% hydroxypropyl methylcellulose (Dow Chemical Pacific Ltd, Marleston, South Australia, Australia) to increase viscosity of the eye drop (Williams et al., *Eye* (2005) 19, 910-913).

Any suitable, e.g., conventional, ophthalmically acceptable carrier may be employed including saline, and other aqueous media, with or without solubility enhancers such as any of the ophthalmically acceptable beta-cyclodextrins. The compounds may be soluble in the carrier which is employed for their administration, so that the compounds are administered to the eye in the form of a solution. Alternatively, a suspension of the compound or compounds (or salts thereof) in a suitable carrier may also be employed. When forming compositions for topical administration, the compounds of the invention are generally formulated as between about 0.001% to 10% w/v, more preferably between about 0.1% to 5% w/v. In one embodiment, the formulation is 1.0% w/v. In one embodiment, the formulations are solutions in water based medium at a pH preferably between about 7.0 to 7.6 pH, preferably pH 7.4±0.3, although the pH may vary. In another aspect of the invention, the compounds are formulated as suspensions.

Tonicity adjusters may be added as needed or convenient. They include, but are not limited to, salts, particularly sodium chloride, potassium chloride etc., mannitol and glycerin, or any other suitable ophthalmically acceptable tonicity adjuster. Such agents, if utilized, will typically be employed in an amount between about 0.1 and about 1.0% by weight.

Various buffers and means for adjusting pH may be used so long as the resulting preparation is ophthalmically acceptable. Accordingly, buffers include but are not limited to, acetate buffers, titrate buffers, phosphate buffers, and borate buffers. Acids or bases may be used to adjust the pH of these formulations as needed. Ophthalmically acceptable antioxidants include, but are not limited to, sodium metabisulfite, sodium thiosulfate, acetylcysteine, butylated hydroxyanisole, and butylated hydroxytoluene. Some compounds may have limited solubility in water and therefore may require a surfactant or other appropriate co-solvent in the composition. Such co-solvents include; Polysorbate 20, 60 and 80; Pluronic F-68, F-84 and P-103; cyclodextrin; polyoxyl 35 castor oil; or other agents known to those skilled in the art. Such co-solvents are typically employed at a level between about 0.01% and about 2% by weight.

Viscosity greater than that of simple aqueous solutions may be desirable to increase ocular absorption of the compound, to decrease variability in dispensing the formulations, to decrease physical separation of components of a suspension or emulsion of formulation and/or otherwise to improve the ophthalmic formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, combinations of the foregoing, and other agents known to those skilled in the art. Such agents are typically employed at a level between about 0.01% and about 2% by weight. Determination of acceptable amounts of any of the above adjuvants is readily ascertained by one skilled in the art.

The ophthalmic solution (ocular drops) may be administered to the mammalian eye as often as necessary. In other words, the ophthalmic solution (or other formulation) is administered to the mammalian eye as often as necessary to maintain the beneficial effect of the active ingredient in the eye. Those skilled in the art will recognize that the frequency of administration depends on the precise nature of the active ingredient and its concentration in the ophthalmic formulation. Within these guidelines it is contemplated that the ophthalmic formulation of the present invention will be administered to the mammalian eye once daily. The formulations may be administered to the mammalian eye anywhere from about 1-4× daily, or as otherwise deemed appropriate by the attending physician. The formulations may also be administered in combination with one or more other pharmaceutical compositions.

The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference.

In addition to the above-described principal ingredients, one skilled in formulating ophthalmic compositions will appreciate that ocular compositions may further comprise various pharmaceutically acceptable ingredients, such as antimicrobial preservatives and tonicity agents. Examples of suitable antimicrobial preservatives include: benzalkonium chloride, thimerosal chlorobutanol, methyl paraben, propyl paraben, phenylethyl alcohol, edetate disodium, sorbic acid, Onamer M® and other agents equally well-known to those skilled in the art. Such preservatives, if utilized, will typically be employed in an amount between about 0.001 and about 1.0 wt %. Examples of suitable agents which may be used to adjust the tonicity or osmolality of the formulations include: sodium chloride, potassium chloride, mannitol, dextrose, glycerin, and propylene glycol. Such agents, if utilized, will typically be employed in an amount between about 0.1 and about 10.0 wt %. Determination of acceptable amounts of the above adjuvants is readily ascertained by one skilled in the art.

As will likewise be appreciated by those skilled in the art, the compositions may be formulated in various dosage forms suitable for topical ophthalmic delivery, as described above, including solutions, suspensions, emulsions, gels, and erodible solid ocular inserts. The compositions are preferably aqueous suspensions or solutions. Further, such formulated compositions may also include one or more additional active ingredients in a single vial for delivery to the patient. One skilled in the art will recognize due care will need to be given in selecting such agents for co-administration from a single formulation with due regard for chemical stability and compatibility with other agents (whether active therapeutic agents or excipients) in the composition made available to the patient.

Small polypeptides including SALLRSIPA (SEQ ID NO:1) and NAPVSIPQ (SEQ ID NO:2) cross the blood brain barrier. For longer polypeptides that do not cross blood brain barrier, methods of administering proteins to the brain are well known. For example, proteins, polypeptides, other compounds and cells can be delivered to the mammalian brain via intracerebroventricular (ICV) injection or via a cannula (see, e.g., Motta & Martini, *Proc. Soc. Exp. Biol. Med.* 168:62-64 (1981); Peterson et al., *Biochem. Pharamacol.* 31:2807-2810 (1982); Rzepczynski et al., *Metab. Brain Dis.* 3:211-216 (1988); Leibowitz et al., *Brain Res. Bull.* 21:905-912 (1988); Sramka et al., *Stereotact. Funct. Neurosurg.* 58:79-83 (1992); Peng et al., *Brain Res.* 632:57-67 (1993); Chem et al., *Exp. Neurol.* 125:72-81 (1994); Nikkhah et al., *Neuroscience* 63:57-72 (1994); Anderson et al., *J. Comp. Neural.* 357:296-317 (1995); and Brecknell & Fawcett, *Exp. Neurol.* 138:338-344 (1996)). In particular, cannulas can be used to administer neurotrophic factors to mammals (see, e.g., Motta & Martini, *Proc. Soc. Exp. Biol. Med.* 168:62-64 (1981) (neurotensin); Peng et al., *Brain Res.* 632:57-67 (1993) (NGF); Anderson et al., *J. Comp. Neurol.* 357:296-317 (1995) (BDNF, NGF, neurotrophin-3).

Drug delivery systems that facilitate transport of drug compounds across the blood brain barrier are known. For example, the methods of the invention can be practiced using LIPOBRIDGE™ (Genzyme Pharmaceuticals) to facilitate transport of longer ADNF polypeptides across the blood brain barrier.

Alternatively, longer ADNF polypeptides that do not cross blood brain barrier can be coupled with a material which assists the ADNF polypeptide to cross the blood brain barrier and to traverse the plasma membrane of a cell, or the membrane of an intra-cellular compartment such as the nucleus. Cellular membranes are composed of lipid-protein bilayers that are freely permeable to small, nonionic lipophilic compounds and are inherently impermeable to polar compounds, macromolecules, and therapeutic or diagnostic agents. However, proteins and other compounds such as liposomes have been described, which have the ability to translocate polypeptides such as ADNF polypeptides across a cell membrane.

For example, "membrane translocation polypeptides" have amphiphilic or hydrophobic amino acid subsequences that have the ability to act as membrane-translocating carriers. In one embodiment, homeodomain proteins have the ability to translocate across cell membranes. The shortest internalizable peptide of a homeodomain protein, Antennapedia, was found to be the third helix of the protein, from amino acid position 42, to 58 (see, e.g., Prochiantz, Current Opinion in Neurobiology 6:629-634 (1996)). Another subsequence, the hydrophobic domain of signal peptides, was found to have similar cell membrane translocation characteristics (see, e.g., Lin et al, J. Biol. Chem. 270:1 4255-14258 (1995)).

Examples of peptide sequences which can be linked to a ADNF polypeptide of the invention, for facilitating uptake of ADNF polypeptides into cells, include, but are not limited to: an 11 amino acid peptide of the tat protein of HIV (see Schwarze et al., Science 285:1569-1572 (1999)); a 20 residue peptide sequence which corresponds to amino acids 84-103 of the p16 protein (see Fahraeus et al., Current Biology 6:84 (1996)); the third helix of the 60-amino acid long homeodomain of Antennapedia (Derossi et al., J. Biol. Chem. 269:10444 (1994)); the h region of a signal peptide such as the Kaposi fibroblast growth factor (K-FGF) h region (Lin et al., supra); or the VP22 translocation domain from HSV (Elliot & O Hare, Cell 88:223-233 (1997), or polyarginine (Chen et al., Chem. Biol. 2001 December; 8(12); 1123-9). Other suitable chemical moieties that provide enhanced cellular uptake may also be chemically linked to ADNF polypeptides.

Toxin molecules also have the ability to transport polypeptides across cell membranes. Often, such molecules are composed of at least two parts (called "binary toxins"), a translocation or binding domain or polypeptide and a separate toxin domain or polypeptide. Typically, the translocation domain or polypeptide binds to a cellular receptor, and then the toxin is transported into the cell. Several bacterial toxins, including *Clostridium perfringens* iota toxin, diphtheria toxin (DT), *Pseudomonas* exotoxin A (PE), pertussis toxin (PT), *Bacillus anthracis* toxin, and pertussis adenylate cyclase (CYA), have been used in attempts to deliver peptides to the cell cytosol as internal or amino-terminal fusions (Arora et al., J. Biol. Chem., 268:3334-3341 (1993); Perelle et al., Infect Immun., 61:5147-5156 (1993); Stenmark et al., J. Cell Biol. 113:1025-1032 (1991); Donnelly et al., Proc. Nat'l Acad. Sci. USA 90:3530-3534 (1993); Carbonetti et al., Abstr. Annu. Meet. Am. Soc. Microbiol. 95:295 (1995); Sebo et al., Infect. Immun. 63:3851-3857 (1995); Klimpel et al., Proc. Nat'l Acad. Sci. USA 89:10277-10281 (1992); and Novak et al., J. Biol. Chem. 267:17186-17193 1992)).

Such subsequences can be used to translocate ADNF polypeptides across a cell membrane. ADNF polypeptides can be conveniently fused to or derivatized with such sequences. Typically, the translocation sequence is provided as part of a fission protein. Optionally, a linker can be used to link the ADNF polypeptides and the translocation sequence. Any suitable linker can be used, e.g., a peptide linker.

The ADNF polypeptides and nucleic acids encoding ADNF polypeptides can also be introduced into an animal cell, preferably a mammalian cell, via a liposomes and liposome derivatives such as immunoliposomes and lipid:nucleic acid complexes. The term "liposome" refers to vesicles comprised of one or more concentrically ordered lipid bilayers, which encapsulate an aqueous phase. The aqueous phase typically contains the compound to be delivered to the cell, i.e., an ADNF polypeptide.

Use of ADNF Polypeptides for Treating Laser-Induced Retinal Damage and Other Conditions Involving Retinal Degeneration As noted above, the present invention provides for the use of ADNF polypeptides, including, for example, NAP, SAL, D-NAP and D-SAL, in the treatment of laser-induced retinal damage (due to, e.g., laser photocoagulation) and other conditions involving retinal degeneration (including, e.g., various ophthalmic diseases, such as glaucoma, ischemic optic neuropathy, and diabetic retinopathy).

In such therapeutic applications, the ADNF polypeptides of the invention are administered to a patient in an amount sufficient to treat laser-induced retinal damage (by, e.g., reducing the spread of such laser-induced retinal damage by secondary degeneration processes) and other conditions involving retinal degeneration. An amount adequate to accomplish this is defined as a "therapeutically effective dose." Amounts effective for this use will depend on, for example, the particular ADNF polypeptide employed, the type of condition, disease or disorder to be prevented, the manner of administration, the weight and general state of health of the patient, and the judgment of the prescribing physician. Prophylactic doses are also encompassed by the terms "therapeutically effective dose."

For example, an amount of polypeptide falling within the range of a 100 ng to 10 mg dose given topically once a day (e.g., as eye drops in the evening) would be a therapeutically effective amount. Alternatively, dosages may be outside of this range, or on a different schedule. For example, dosages may range from 0.0001 mg/kg to 1000 mg/kg, and will preferably be about 0.001 mg/kg, 0.1 mg/kg, 1 mg/kg, 5 mg/kg, 50 mg/kg or 500 mg/kg per dose. Doses may be administered hourly, every 4, 6 or 12 hours, with meals, daily, every 2, 3, 4, 5, 6, or 7 days, weekly, every 2, 3, 4 weeks, monthly or every 2, 3 or 4 months, or ally combination thereof. The duration of dosing may be single (acute) dosing, or over the course of days, weeks, months, or years, depending on the condition to be treated. Those skilled in the art can determine the suitable dosage, and may rely on preliminary data reported in Gozes et al., 2000, Gozes et al., 2002), Bassan et al. 1999; Zemlyak et al., *Regul. Pept.* 96:39-43 (2000); Brenneman et al., *Biochem. Soc. Trans.* 28; 452-455 (2000); *Erratum Biochem Soc. Trans.* 28:983; Wilkemeyer et al. *Proc. Natl. Acad. Sci. USA* 100: 8543-8548 (2003)). Suitable dose ranges are described in the examples provided herein, as well as in International PCT Publication No. WO 96/11948.

With respect to the administration of an ADNF polypeptide to treat laser-induced retinal damage, administration may occur before, at the same time as, and/or subsequent to the occurrence of the primary injury or damage. Treatment may continue until the primary lesion is healed, or until such time as the primary lesion is not expected to worsen. Similarly, with respect to the administration of an ADNF polypeptide to treat other conditions involving retinal degeneration, such as various ophthalmic diseases (e.g., glaucoma, ischemic optic neuropathy, and diabetic retinopathy), administration may occur before, at the same time as, and/or subsequent to the onset of the retinal degeneration in a subject suffering from such a condition. Treatment may continue until the underlying condition resolves, or until the retinal degeneration resulting from the condition is resolved and not expected to worsen. In some cases, administration of ADNF polypeptides may be chronic.

It must be noted that as used herein and in the appended claims, the singular forms "a", "and", and "the" include plural referents unless the context clearly dictates otherwise. Thus, for example, reference to "a cell" includes a plurality of such cells and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed. In addition, all citations are incorporated herein by reference in their entirety.

EXAMPLES

The present study tested the neuroprotective ability of NAP to reduce the spread of laser-induced retinal damage by secondary retinal degeneration processes.

Example 1

Treatment of Laser Injury with NAP

Materials and Methods

Animals

A total of 72 rats in four experimental groups were used for the research: 36 rats in two groups (I and II) of NAP neuroprotective effect evaluation, and 36 rats in two control groups (III and IV) (see Table 1 below).

Pigmented DA rats (strain DA/Ola/Hsd, Harlan OCAL Ltd., Blackthorn Bicester Oxon, England; raised in Tel-Aviv University animal house), 90 days old, were used for the experiments. The posterior segment of the eye of this strain has a uniform pigmentation, making it particularly useful for retinal laser injury production. The animals were fed ad libitum with a normal laboratory diet and maintained on a 12-h light/dark cycle. They were anesthetized by intraperitoneal injections of ketamine (40 mg/kg) and xylasine (8 mg/kg) before each experimental procedure.

TABLE 1

Animal groups and research progress

| # | Number of animals | Title of group | |
|---|---|---|---|
| I | 18 | NAP systemic | NAP injected systemically (intravenously) |
| II | 18 | NAP local | NAP injected locally (intravitreally) |
| III | 18 | Control systemic | Control group, saline injected systemically (intravenously) |
| IV | 18 | Control local | Control group, saline injected locally (intravitreally) |

Protocols

1. Laser Injury

After dilatation of the pupil with sterile drops of Topicamid 0.5% (Midramid, Fisher), a contact lens, specially crafted to fit a rat eye for retinal laser irradiation, was attached to the cornea with 2.5% hydroxypropyl methylcellulose. Six laser retinal lesions were produced in each eye of each of the anesthetized (ketamine (40 mg/kg) and xylasine (8 mg/kg)) rats by argon laser (Novus 2000 Coherent, CA) two disc diameters away from the optic disc. The laser beam characteristics were 514 & 544 nm, 200 μm, 0.1 W, 0.05 second. These laser settings were found in previous studies to result in lesions of a uniform size and configuration, involving mainly the outer retinal layers.

2. Intravenous Injection

The animals of the experimental groups I and III underwent systemic intravenous injection of NAP or saline immediately after the laser photocoagulation, NAP was injected in the amount of 60 μg per animal (about 280-300 μg/kg) in a volume of 0.5 ml of saline. The animals of the control group got an injection of 0.5 ml of saline. The injections were performed in the femoral vein of the right leg of each animal after the vessel was uncovered and isolated in situ. The wound was sewed up after the injection with surgical silk.

3. Intravitreal Injection

The animals of the experimental groups II and IV underwent NAP or saline injection immediately after the laser photocoagulation. Each eye of each anesthetized rat was punctured with a 30-gauge needle of a Hamilton syringe at the temporal posterior part of the retina. Then, 5 μl of NAP saline solution at a concentration of 2.5 pg/μl was injected into the vitreous body of the experimental group. The same amount of saline (5 μl) was injected intravitreally in the animals of the control groups. All of the procedures were controlled visually via a surgical microscope.

4. Histopathologic and Morphometric Studies

The effect of treatment in all groups was evaluated at three time points: 3, 20, and 60 days after the primary injury (n=6 at each time point in each group). The animals were euthanized by a lethal dose of pentobarbitone and their eyes enucleated and fixed in 2% glutaraldehyde. Using a surgical microscope, the posterior segment of the fixed eye was dissected into tissue samples, each incorporating one retinal laser lesion. The samples were embedded in epoxy resin and the blocks sectioned serially (1 μm) with an ultramicrotome and stained with toluidine blue. The sections from the central part of the lesion, exhibiting the greatest degree of laser-induced retinal destruction, were examined by light microscopy for histopathological changes.

The microscopic images were digitalized by SmartCapture VP software (Digital Scientific, USA) and enhanced by IPLab software (Scanalytics, USA). Then the images were segmented for photoreceptor clarification by IPLab software (Scanalytics, USA) and the photoreceptors were counted.

Morphometric measurements were performed on each lesion in order to evaluate the severity of the argon laser injury. The borders of the lesion area were established at the most distant point from the middle of the lesion where the cytoarchitecture changes in the pigment epithelium, outer nuclear, inner nuclear, or ganglion cell layers of the retina could be distinguished. The measurements performed were: 1) Diameter of the whole lesion, 2) Cell count in the outer nuclear layer of the whole lesion area, and 3) Cell count in the outer nuclear layer at the 100 μm center of the lesion In order to evaluate the extent of photoreceptor cell loss, results were compared to the cell density in the intact regions of the outer nuclear retinal layer located 100 μm peripherally from the edges of the lesion.

5. Calculations and Statistical Analysis

Every slide was processed twice and all the measurements were done in triplicate. Means±SD were used to describe the various parameters; two-ways ANOVA was applied to detect significant difference between the various groups.

Results

From 432 laser injuries, 288 slides (four for each animal) were selected for the further image processing and 576 digitalized images (each slide twice) were analyzed to evaluate the neuroprotective effect NAP administered in two different ways (systemic aid intravitreal) versus two corresponding control groups.

Figure 1B:
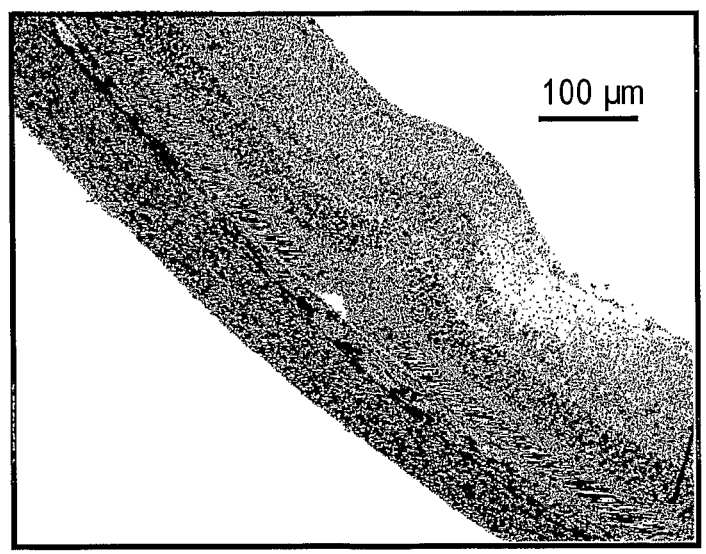
Figure 1C:
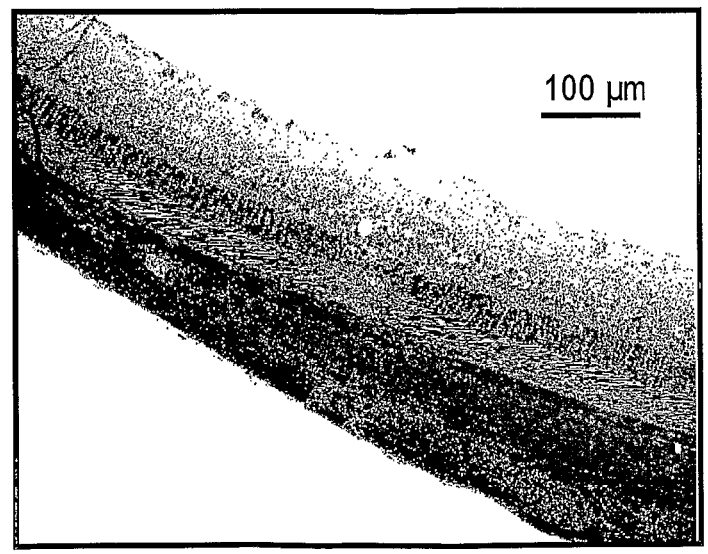

FIGS. 1a-1c show exemplary microscopic views of an untreated laser lesion 3, 20 and 60 days after laser irradiation. The histological evaluation three days after the laser irradiation (FIG. 1a) showed that the outer and inner segments of the photoreceptors were deformed and disrupted and the outer nuclear layer (ONL) showed loss of nuclei. The photoreceptor cells were absent in the center of the lesion which was filled with cellular debris. The outer plexiform layer was disrupted and the whole retina was edematous. By 20 days after laser exposure (FIG. 1b), the retinal pigment epithelium (RPE) layer moved to its initial position and was lying on the subretinal membrane. The inner nuclear layer was still edematous, causing the nerve fiber layer to be folded internally. By 60 days after the laser injury (FIG. 1c), the subretinal membranes had diminished in size, become fibrotic, and contained small blood vessels. The outer and inner segments of photoreceptors were disrupted in the central area of the lesion, but the gap in the continuity of the retina had diminished.

Neuroprotective Effect of Systemic NAP Administration

Figure 2:
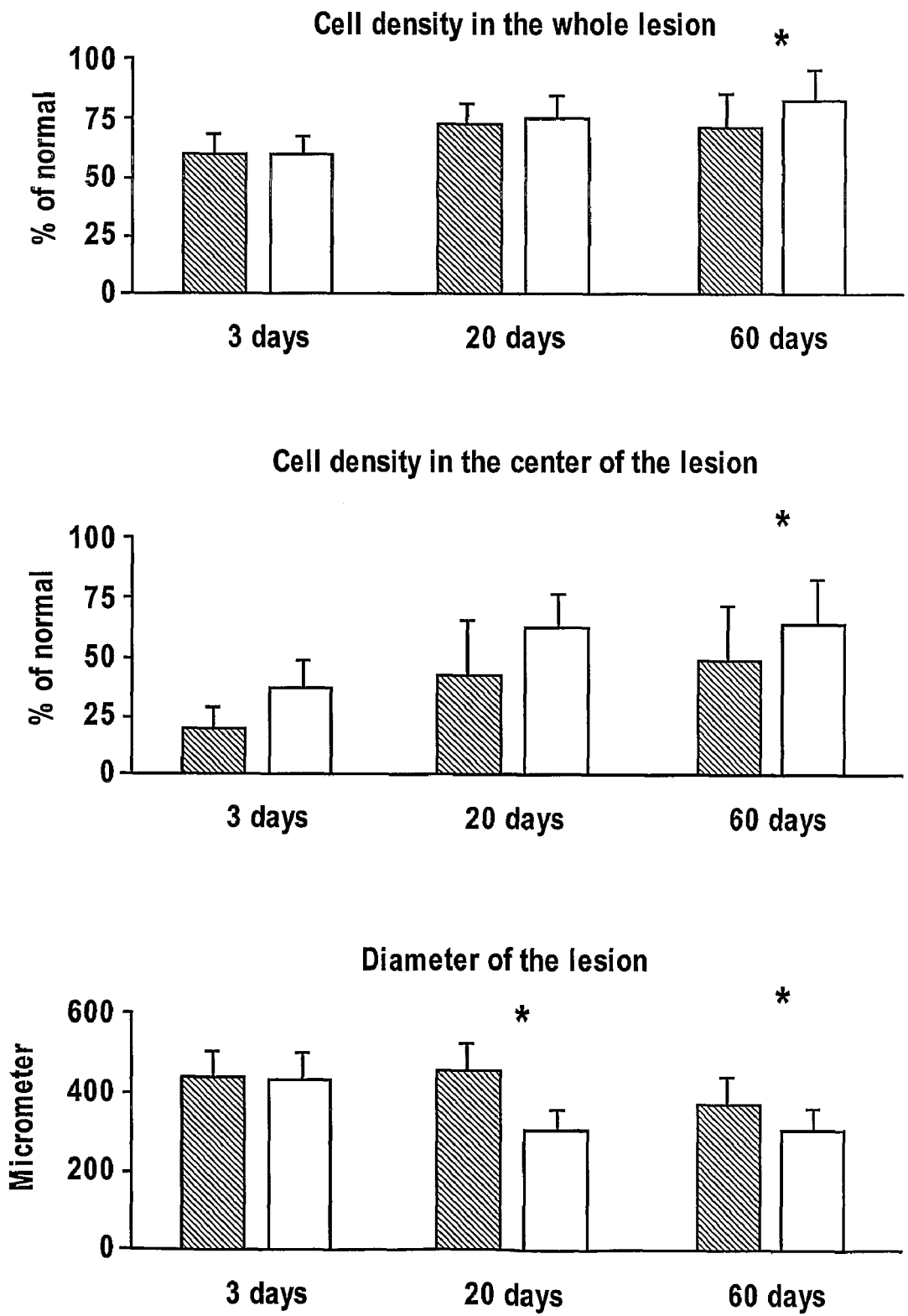
FIG. 2 shows the morphometric parameters (mean±STD) after systemic administration of NAP (light bars) and saline (dark bars). Asterisks mark significant differences between experimental and control groups (P<0.05).

Morphological evaluations of the lesions 3 and 20 days after the injury revealed attenuation in photoreceptor loss and lesion diameter in the treated animals as compared to the control groups (FIG. 2). This neuroprotective effect was also manifested, although to a lesser extent, 60 days after the laser session.

Measured 3, 20, and 60 days after injury, the number of cells lost was reduced by treatment with NAP, both in the whole and central areas, though only sixty days after photocoagulation was his reduction statistically significant ($P<0.01$).

The systemic administration of NAP had significant ameliorative effects ($P<0.01$) on the diameter of the lesion 20 and 60 days after the injury.

Neuroprotective Effect of Intravitreal NAP Administration

Morphological observation could not define the difference between the lesions in the eyes of animals treated systemically and intravitreally. The puncture point of injection could be detected easily on the posterior retina. In some eyes, the intravitreal injection caused inflammation and fibrinigenesis. On several other eyes, the lens was damaged during the injection and, subsequently, cataract developed. Animals with such complications due to the intravitreal injection were excluded from the study.

Figure 3:
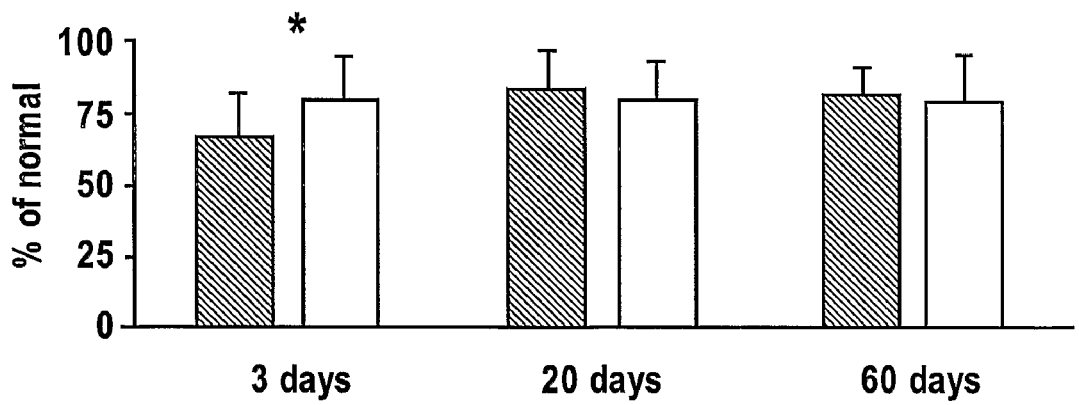
FIG. 3 shows the morphometric parameters (mean±STD) after intravitreal administration of NAP (light bars) and saline (dark bars). Asterisks mark significant differences between experimental and control groups (P<0.05).
Figure 3:
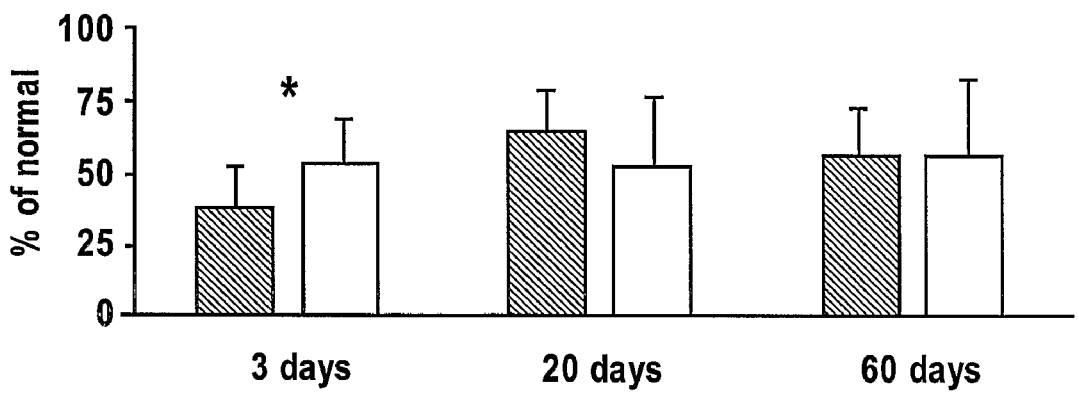
Figure 3:
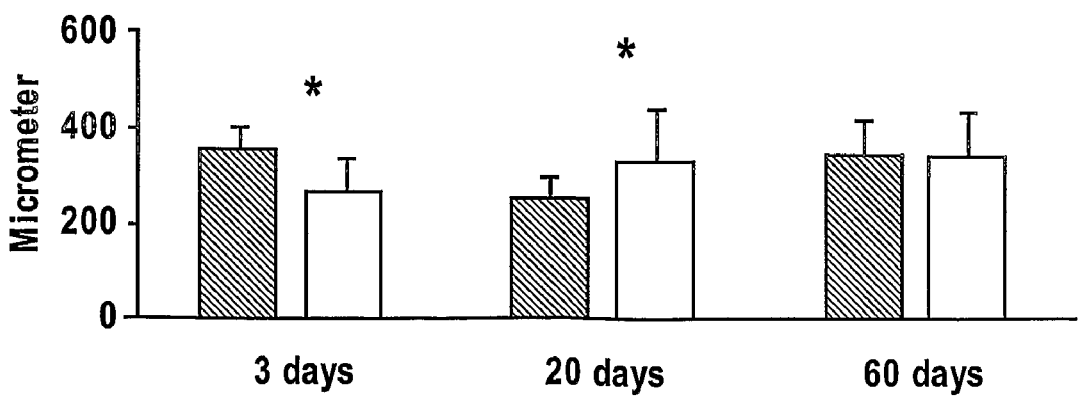

The significant neuroprotective effect of NAP intravitreal administration against laser-induced retinal damage was only seen 3 days after the laser session ($P<0.05$), and not after 20 and 60 days (FIG. 3). Similarly, the mean lesion diameter was reduced in the eyes treated with NAP 3 days after the laser injury, but after 20 days the mean lesion diameter was greater than in control groups.

Example 2

Topical Administration of NAP Via Eye Drops

Methods

Three albino rabbits (each three months old) were used. One animal at a time was anesthetized using Ketamin (40 mg/kg) and Xylazine (8 mg/kg). After the animals were fully anesthetized, a drop of radioactive drug—$^{14}$C-NAPVSIPQ (SEQ ID NO:24) (50 microliter; $1.5 \times 10^6$ dpm; 37 mCi/mmol; 1 microCi=$2 \times 10^6$ dpm) was applied once by a micropipette to each eye, i.e., eye drops. The eye drops were prepared to include 2.7 microliter of the $^{14}$C-NAP stock in 400 microliter saline (0.9% NaCl). 10 microliters of this solution were counted to yield $3 \times 10^5$ dpm. After application of the drug, eye lids were held gently closed for 10 seconds.

The aqueous humor is the liquid that is found in-between the cornea and lens. Ten microliter samples of aqueous humor were taken from the rabbits' eyes using a tuberculin syringe with a 30 gauge needle.

The vitreous humor is found between the retina and the lens. Vitreous samples were obtained through the pars plana with a 25 gauge needle attached to a Tuberculin syringe. Ten microliter samples of vitreous humor were taken from each eye at designated times as outlined in the attached graphs up to 130 minutes after the initial eye drop application Systemic samples were taken from blood. For results see, e.g., FIGS. 4-6.

The animals were anesthetized for the duration of the tidal to avoid animal suffering. A boost of anesthetics was injected about ninety minutes after the initiation of the experiment.

Results

Figure 4:
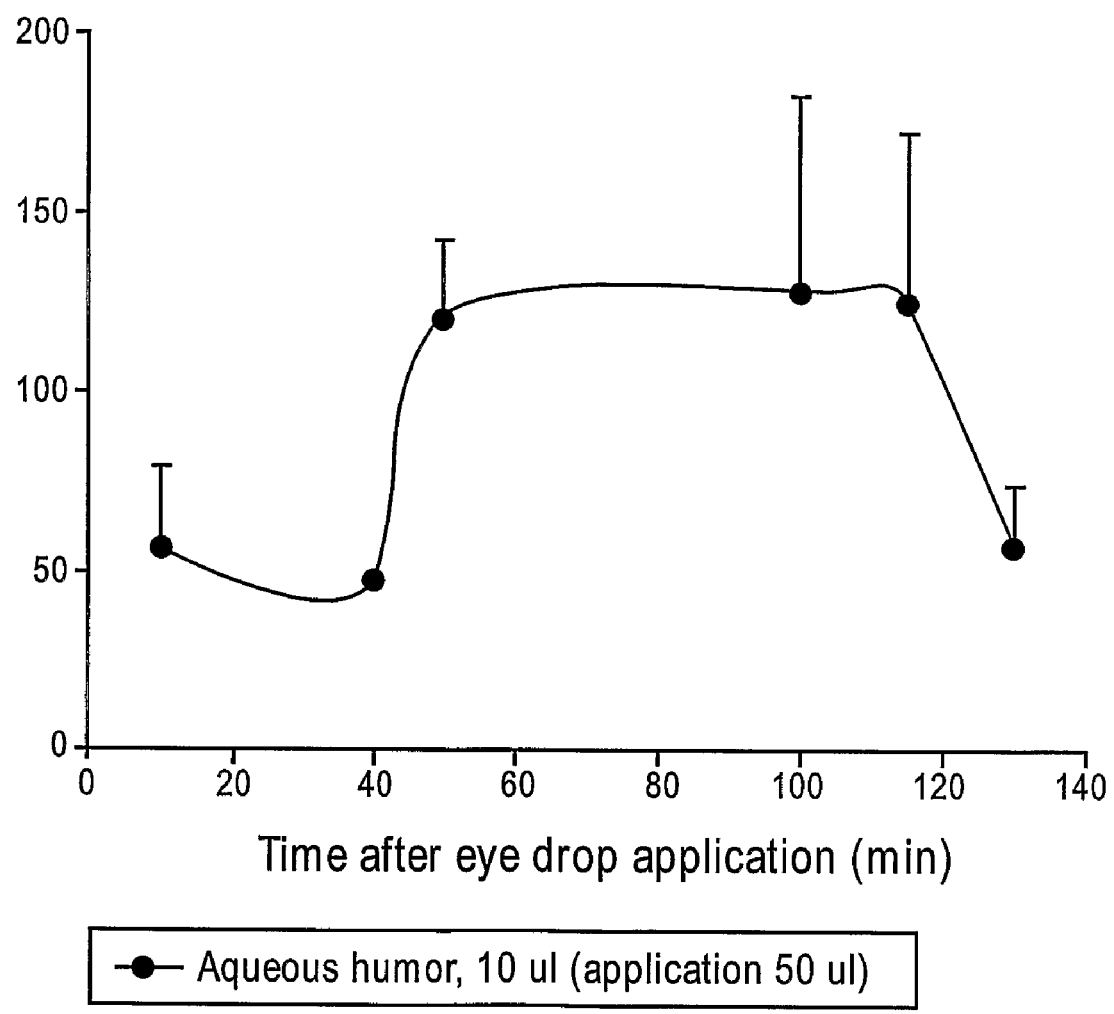
FIG. 4 shows a time course of incorporation of radiolabeled NAP into the aqueous humor after topical administration (eye drop) to the eye of a rabbit.
Figure 5:
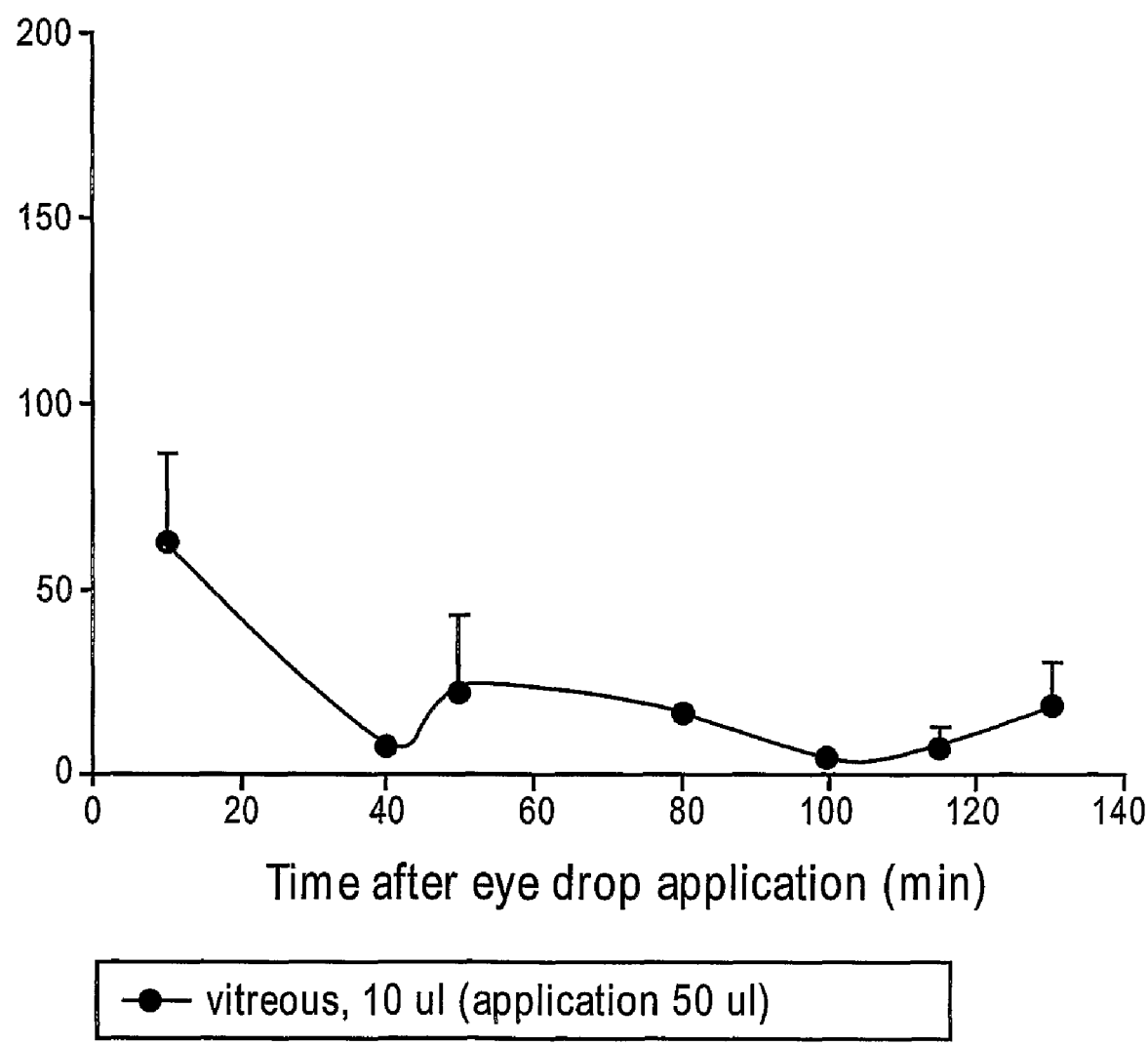
FIG. 5 shows a time course of incorporation of radiolabeled NAP into the vitreous humor after topical administration (eye drop) to the eye of a rabbit.
Figure 6:
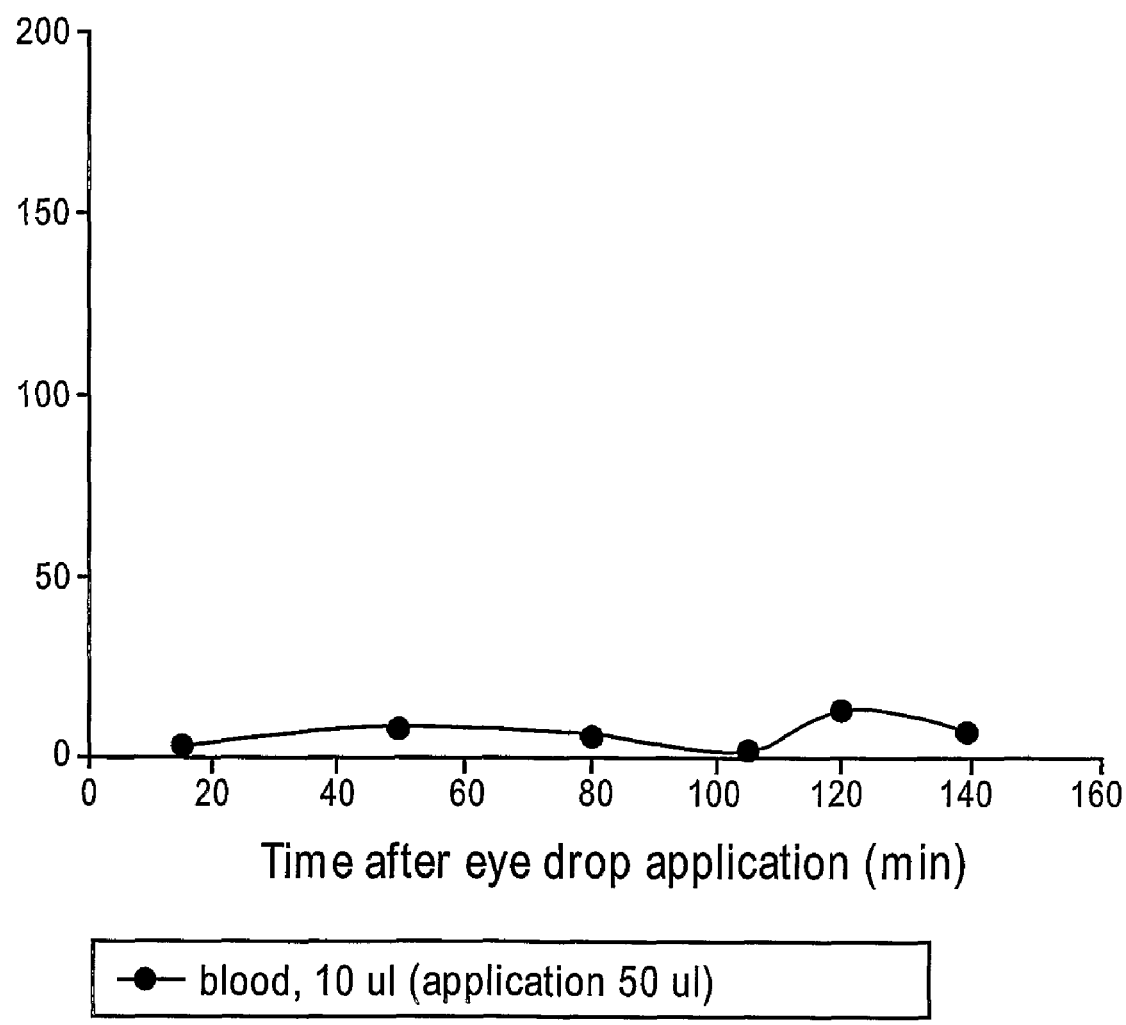
FIG. 6 shows a time course of incorporation of radiolabeled NAP into the systemic blood stream after topical administration (eye drop) to the eye of a rabbit.

A peak of radioactive incorporation into the aqueous humor was obtained 50 minutes after the initial application (150 dpm/10 microliter, and was maintained for 70 minutes (up to 120 minutes after the initial application). The results shown in FIG. 4 summarize three animals—six eyes. FIG. 5 shows the results for the vitreous samples, here maximal incorporation was observed 10 minutes after application and amounted to 60 dpm/10 microliters, similar to the amount of radioactivity observed at the aqueous humor at the 10 minute point after eye drop application. There was almost no systemic exposure (FIG. 6, 1-12 dpm for all time points). A control reading, 10 microliter saline, was $\leq$10 dpm.

Topical administration of NAP to the eye results in local incorporation of the drag for use as a therapeutic at that site.

Example 2

Administration of NAP in an Animal Model of Pan Retinal Photocoagulation Methods Thirty-six pigmented DA male rats (strain DA/Ola/Hsd, Harlan OCAL LTd./Blackthorn Bicester Oxen, England; raised in Tel-Aviv University animal house), 90 days old, were used in this study.

The study group will consisted of 36 animals; one eye of each was lased as above. Half of the animals were given 60 μgm AL-208 in 0.5 ml of saline intravenously immediately prior to the lasing and half will received an equivalent amount of saline.

ERG was performed on all animals in a masked fashion at 3 and 20 days after the lasering. Experiments are also done at 60 days after the lasering.

Laser Injury

The animals were anesthetized (intramuscular injection of 20 mg ketamine and 1 mg xylasine) and after dilation of the pupil with sterile drops of Topicamid 0.5% (Midramid, Fisher), a contact lens, specially crafted in our Institute, to fit a rat eye for retinal laser irradiation, was attached to the cornea with 2.5% hydroxypropyl methylcellulose. Argon laser (Novus 2000 Coherent, CA, the laser used for performing PRP on patients) was used to create standard argon lesions in the right eye of the experimental animals. The laser settings were: 514 & 544 nm, 200 μm spot at 0.1 W for 0.05 seconds. These settings were found in previous studies to result in lesions of uniform size and configuration, involving mainly the outer retinal layers. The lesions numbered about 225 lesions per eye, covering the entire visible retina in the nasal hemifield. All lesions were induced in the right eye and the left eye served as a normal control for the electrophysiological measurements.

Flash ERG Recording

The flash (ERG) was used to assess changes in outer retinal function of the lased right eyes, relative to the control left eyes. Recordings were or will be conducted in both eyes (sequentially) 3, 20 and 60 days after laser injury; the order of the eyes recorded will be random. Recordings were or will be performed by an investigator masked regarding the identity of the experimental groups.

Rats were or will be anesthetized using an intramuscular injection of 20 mg ketamine and 1 mg xylazine, and their pupils dilated. They were or will be placed in a Faraday cage on a warm water-heating pad. Animals were or will be dark-adapted for ten minutes prior to the beginning of recording. White stroboscopic stimulus were or will be delivered at a frequency of 0.1 Hz, using a xenon flash stimulator (Nicolet Biomedical Inc., Madison, Wis., USA). Retinal signals were or will be recorded using a contact lens electrode designed for use in rats (Medical Workshops, Groningen, Netherlands).

Subcutaneous needles were or will serve both as reference and as ground electrodes, and were or will be placed at the temporal canthus of the ipsilateral eye and at the base of the ear, respectively. Signals were or will be amplified with a 2-250 Hz band-pass (Without notch filter), averaged online (n=10) and stores for subsequent analysis. The effect of the lasering on b-wave was or will be measured by the ratio between the right (lasered) eye and the left (intact) eye at the 3, 20 and 60 days after lasering. Evaluation of lasering was or will be assessed using a paired Student's t-test. P-values <0.05 will be considered significant.

Morphological Assessment of Retinal Damage Caused by Laser

The laser lesions were or will be evaluated histologically and morphologically 60 days after the injury (8 animals of each group). The animals were or will be euthanized by a lethal dose of pentobarbitone and their eyes enucleated and fixed in 2% glutaraldehyde. Using a surgical microscope, the posterior segment of the fixed eye was or will be dissected into tissue samples, each incorporating one retinal laser lesion. The samples were or will be embedded in epoxy resin and blocks sectioned serially (1 μm) with an ultramicrotome and stained with toluidine blue. The sections of the photocoagulated area of retina were or will be examined by light microscopy for histopathological changes.

Results

NAP (AL-208) protected against functional loss in the laser-damaged eye by ERG measurements—performed 3 and 20 days after the damage/treatment. Similar results are expected at the 60 day time point.

The examples set out above are intended to be exemplary of the effects of the invention, and are not intended to limit the embodiments or scope of the invention contemplated by the claims set out below. Other variants of the invention will be readily apparent to one of ordinary skill in the art and are encompassed by the appended claims. All publications, databases, Genbank sequences, GO terms, patents, and patent applications cited herein are hereby incorporated by reference.

What is claimed is:

1. A method for treating retinal damage in a subject whose retina has been directly damaged by laser, the method comprising administering a therapeutically effective amount of an ADNF polypeptide to a subject in need thereof, wherein the ADNF polypeptide is a member selected from the group consisting of:
    (a) an ADNF I polypeptide comprising an active-core site having the following amino acid sequence: Ser-Ala-Leu-Leu-Arg-Ser-Ile-Pro-Ala (SEQ ID NO:1);
    (b) an ADNF III polypeptide comprising an active core site having the following amino acid sequence: Asn-Ala-Pro-Val-Ser-Ile-Pro-Gln (SEQ ID NO:2); and
    (c) a mixture of the ADNF I polypeptide of part (a) and the ADNF III polypeptide of part (b).

2. The method of claim 1, wherein the retina being directly damaged by laser is a consequence of laser photocoagulation.

3. The method of claim 1, wherein the retina being directly damaged by laser is a consequence of an accident.

4. The method of claim 1, wherein the ADNF polypeptide is administered intranasally, orally, intravenously, subcutaneously, or intravitreally.

5. The method of claim 1, wherein the ADNF polypeptide is administered topically.

6. The method of claim 1, wherein the ADNF polypeptide is a member selected from the group consisting of a full length ADNF I polypeptide, a full length ADNF III polypeptide (ADNP), and a mixture of a full length ADNF I polypeptide and a full length ADNF III polypeptide.

7. The method of claim 1, wherein the ADNF polypeptide is an ADNF I polypeptide.

8. The method of claim 7, wherein the active core site of the ADNF I polypeptide comprises at least one D-amino acid.

9. The method of claim 7, wherein the ADNF I polypeptide has the formula $(R^1)_x$-Ser-Ala-Leu-Leu-Arg-Ser-Ile-Pro-Ala-$(R^2)_y$ (SEQ ID NO:27) in which:
    $R^1$ is an amino acid sequence comprising from 1 to about 40 amino acids wherein each amino acid is independently selected from the group consisting of naturally occurring amino acids and amino acid analogs;
    $R^2$ is an amino acid sequence comprising from 1 to about 40 amino acids wherein each amino acid is independently selected from the group consisting of naturally occurring amino acids and amino acid analogs; and
    x and y are independently selected and are equal to zero or one.

10. The method of claim 9, wherein the ADNF I polypeptide is Ser-Ala-Leu-Leu-Arg-Ser-Ile-Pro-Ala (SEQ ID NO:1).

11. The method of claim 9, wherein the ADNF I polypeptide is selected from the group consisting of:
    Val-Leu-Gly-Gly-Gly-Ser-Ala-Leu-Leu-Arg-Ser-ILe-Pro-Ala (SEQ ID NO:3);
    Val-Glu-Glu-Gly-Ile-Val-Leu-Gly-Gly-Gly-Ser-Ala-Leu-Arg-Ser-Ile-Pro-Ala (SEQ ID NO:4);
    Leu-Gly-Gly-Gly-Ser-Ala-Leu-Leu-Arg-Ser-Ile-Pro-Ala (SEQ ID NO:5);
    Gly-Gly-Gly-Ser-Ala-Leu-Leu-Arg-Ser-Ile-Pro-Ala (SEQ ID NO:6);
    Gly-Gly-Ser-Ala-Leu-Leu-Arg-Ser-Ile-Pro-Ala (SEQ ID NO:7);
    Gly-Ser-Ala-Leu-Leu-Arg-Ser-Ile-Pro-Ala (SEQ ID NO:8); and
    Ser-Ala-Leu-Leu-Arg-Ser-Ile-Pro-Ala (SEQ ID NO:1).

12. The method of claim 9, wherein the ADNF I polypeptide comprises up to about 20 amino acids at either or both of the N-terminus and the C-terminus of the active core site.

13. The method of claim 1, wherein the ADNF polypeptide is an ADNF III polypeptide.

14. The method of claim 13, wherein the active core site of the ADNF III polypeptide comprises at least one D-amino acid.

15. The method of claim 13, wherein the ADNF III polypeptide has the formula $(R^1)_x$-Asn-Ala-Pro-Val-Ser-Ile-Pro-Gln-$(R^2)_y$ (SEQ ID NO:13) in which:

R¹ is an amino acid sequence comprising from 1 to about 40 amino acids wherein each amino acid is independently selected from the group consisting of naturally occurring amino acids and amino acid analogs;

R² is an amino acid sequence comprising from 1 to about 40 amino acids wherein each amino acid is independently selected from the group consisting of naturally occurring amino acids and amino acid analogs; and x and y are independently selected and are equal to zero or one.

16. The method of claim 15, wherein the ADNF III polypeptide is Asn-Ala-Pro-Val-Ser-Ile-Pro-Gln (SEQ ID NO:2).

17. The method of claim 15, wherein the ADNF III polypeptide is a member selected from the group consisting of:
Gly-Gly-Asn-Ala-Pro-Val-Ser-Ile-Pro-Gln (SEQ ID NO:9);
Leu-Gly-Gly-Asn-Ala-Pro-Val-Ser-Ile-Pro-Gln-Gln-Ser (SEQ ID NO:10);
Leu-Gly-Leu-Gly-Gly-Asn-Ala-Pro-Val-Ser-Ile-Pro-Gln-Gln-Ser (SEQ ID NO:11);
Ser-Val-Arg-Leu-Gly-Leu-Gly-Gly-Asn-Ala-Pro-Val-Ser-Ile-Pro-Gln-Gln-Ser (SEQ ID NO:12); and
Asn-Ala-Pro-Val-Ser-Ile-Pro-Gln (SEQ ID NO:2).

18. The method of claim 15, wherein the ADNF III polypeptide comprises up to about 20 amino acids at either or both of the N-terminus and the C-terminus of the active core site.

19. The method of claim 1, wherein a mixture of the ADNF I polypeptide of part (a) and the ADNF III polypeptide of part (b) is administered to the subject.

20. The method of claim 19, wherein either or both active core sites of the ADNF I polypeptide and the ADNF III polypeptide comprise at least one D-amino acid.

21. The method of claim 19, wherein the ADNF I polypeptide is Ser-Ala-Leu-Leu-Arg-Ser-Ile-Pro-Ala (SEQ ID NO:1), and wherein the ADNF III polypeptide is Asn-Ala-Pro-Val-Ser-Ile-Pro-Gln (SEQ ID NO:2).

22. The method of claim 19, wherein the ADNF I polypeptide is a member selected from the group consisting of:
Val-Leu-Gly-Gly-Gly-Ser-Ala-Leu-Leu-Arg-Ser-ILe-Pro-Ala (SEQ ID NO:3);
Val-Glu-Glu-Gly-Ile-Val-Leu-Gly-Gly-Gly-Ser-Ala-Leu-Leu-Arg-Ser-Ile-Pro-Ala (SEQ ID NO:4);
Leu-Gly-Gly-Gly-Ser-Ala-Leu-Leu-Arg-Ser-Ile-Pro-Ala (SEQ ID NO:5);
Gly-Gly-Gly-Ser-Ala-Leu-Leu-Arg-Ser-Ile-Pro-Ala (SEQ ID NO:6);
Gly-Gly-Ser-Ala-Leu-Leu-Arg-Ser-Ile-Pro-Ala (SEQ ID NO:7);
Gly-Ser-Ala-Leu-Leu-Arg-Ser-Ile-Pro-Ala (SEQ ID NO:8); and
Ser-Ala-Leu-Leu-Arg-Ser-Ile-Pro-Ala (SEQ ID NO:1); and
wherein the ADNF III polypeptide is selected from the group consisting of:
Gly-Gly-Asn-Ala-Pro-Val-Ser-Ile-Pro-Gln (SEQ ID NO:9);
Leu-Gly-Gly-Asn-Ala-Pro-Val-Ser-Ile-Pro-Gln-Gln-Ser (SEQ ID NO:10);
Leu-Gly-Leu-Gly-Gly-Asn-Ala-Pro-Val-Ser-Ile-Pro-Gln-Gln-Ser (SEQ ID NO:11);
Ser-Val-Arg-Leu-Gly-Leu-Gly-Gly-Asn-Ala-Pro-Val-Ser-Ile-Pro-Gln-Gln-Ser (SEQ ID NO:12); and
Asn-Ala-Pro-Val-Ser-Ile-Pro-Gln (SEQ ID NO:2).

23. The method of claim 19, wherein the ADNF I polypeptide comprises up to about 20 amino acids at either or both of the N-terminus and the C-terminus of the active core site of the ADNF I polypeptide, and wherein the ADNF III polypeptide comprises up to about 20 amino acids at either or both of the N-terminus and the C-terminus of the active core site of the ADNF III polypeptide.

* * * * *